(12) United States Patent
Blackman et al.

(10) Patent No.: US 7,811,782 B2
(45) Date of Patent: Oct. 12, 2010

(54) USE OF AN IN VITRO HEMODYNAMIC ENDOTHELIAL/SMOOTH MUSCLE CELL CO-CULTURE MODEL TO IDENTIFY NEW THERAPEUTIC TARGETS FOR VASCULAR DISEASE

(75) Inventors: Brett R. Blackman, Charlottesville, VA (US); Brian R. Wamhoff, Charlottesville, VA (US)

(73) Assignee: Hemoshear, LLC, Charlottesville, VA (US)

( * ) Notice: Subject to any disclaimer, the term of this patent is extended or adjusted under 35 U.S.C. 154(b) by 159 days.

(21) Appl. No.: 12/007,483

(22) Filed: Jan. 10, 2008

(65) Prior Publication Data

US 2009/0053752 A1 Feb. 26, 2009

Related U.S. Application Data

(60) Provisional application No. 60/879,710, filed on Jan. 10, 2007.

(51) Int. Cl.
*C12Q 1/02* (2006.01)
*C12N 5/07* (2010.01)
*C12N 5/00* (2010.01)
(52) U.S. Cl. .................... 435/29; 435/347; 435/373; 435/395; 435/401
(58) Field of Classification Search ................ None
See application file for complete search history.

(56) References Cited

OTHER PUBLICATIONS

Cattaruzza et al. Shear Stress Insensitivity of Endothelial Nitric Oxide Synthase Expression As a Genetic Risk Factor for Coronary Heart Disease; Circulation Research, vol. 95 (2004) pp. 841-847.*
Starmans-Kool et al. Measurement of Hemodynamics in Human Carotid Artery Using Ultrasound and Computational Fluid Dynamics; Journal of Applied Physiology, vol. 92 (2002) pp. 957-961.*
Malek et al. A Cone-Plate Apparatus for the In Vitro Biochemical and Molecular Analysis of the Effect of Shear Stress on Adherent Cells, Methods of Cell Science, vol. 17 (1995) pp. 165-176.*
Chiu et al. Shear Stress Inhibits Adhesion Molecule Expression in Vascular Endothelial Cells Induced by Coculture With Smooth Muscle Cells; Blood, vol. 101, No. 7 (2003) pp. 2667-2674.*
Navab et al. Monocyte Migration Into the Subendothelial Space of a Coculture of Adult Human Aortic Endothelial and Smooth Muscle Cells; Journal of Clinical Investigation, vol. 82 (1988) pp. 1853-1863.*
Gerthoffer et al. Secretory Functions of Smooth Muscle: Cytokines and Growth Factors; Molecular Interventions, vol. 2, No. 7 (2002) pp. 448-456.*
Wilczek et al. Comparison of Self-Expanding Polyethylene Terephthalate and Metallic Stents Implanted in Porcine Iliac Arteries; Cardiovascular and Interventional Radiology, vol. 19 (1996) pp. 176-180.*
Blackman, Brett R., A New In Vitro Model to Evaluate Differential Responses of Endothelial Cells to Simulated Arterial Shears Stress Waveforms, Journal of Biomechanical Engineering, Aug. 2002, pp. 397-407, Boston, MA.
Chiu, Jeng-Jiann, A Model for Studying the Effect of Shear Stress on Interactions Between Vascular Endothelial Cells and Smooth Muscle Cells, Journal of Biomechanical Engineering, Aug. 2003, pp. 351-539, Taipei, Taiwan, ROC.
Cunningham, Kristopher S., The Role of Shear Stress in the Pathogenesis of Atherosclerosis, Laboratory Investigation, Nov. 29, 2004, pp. 9-23, Toronto, Ontario, Canada.
Hastings, Nicole E., Atherosclerosis-Prone Hemodynamics Differentially Regulates Endothelial and Smooth Muscle Cell Phenotypes and Promotes Pro-Inflammatory Priming, AJP Cell Physiology, Oct. 2, 2007, pp. 1824-1833, Bethesda, MD.

* cited by examiner

*Primary Examiner*—Rebecca E. Prouty
*Assistant Examiner*—Paul C. Martin
(74) *Attorney, Agent, or Firm*—Senniger Powers LLP

(57) ABSTRACT

Methods and devices for applying hemodynamic patterns to human/animal cells in culture are described. Hemodynamic flow patterns are measured directly from the human circulation and translated to a motor that controls the rotation of a cone. The cone is submerged in fluid (i.e., cell culture media) and brought into close proximity to the cells. Rotation of the cone creates time-varying shear stresses. This model closely mimics the physiological hemodynamic forces imparted on endothelial cells in vivo. A TRANSWELL coculture dish (i.e., a coculture dish comprising an artificial porous membrane) may be incorporated, permitting two, three, or more different cell types to be physically separated within the culture dish environment. In-flow and out-flow tubing may be used to supply media, drugs, etc. separately and independently to both the inner and outer chambers. The physical separation of the cell types permits each cell type to be separately isolated for analysis.

43 Claims, 19 Drawing Sheets

USE OF AN IN VITRO HEMODYNAMIC ENDOTHELIAL/SMOOTH MUSCLE CELL CO-CULTURE MODEL TO IDENTIFY NEW THERAPEUTIC TARGETS FOR VASCULAR DISEASE

CROSS REFERENCE TO RELATED APPLICATIONS

This application claims priority under 35 U.S.C. §119(e) from U.S. Provisional Patent Application No. 60/879,710, filed on Jan. 10, 2007, which is incorporated herein by reference.

STATEMENT REGARDING SPONSORED RESEARCH OR DEVELOPMENT

Not Applicable.

REFERENCE TO SEQUENCE LISTING

Not Applicable.

BACKGROUND OF THE INVENTION

1. Field of the Invention

This invention relates generally to devices and methods for in vitro analysis of fluid flow (e.g., hemodynamics) on cells (e.g., endothelial cells). More specifically, this invention relates to a method of using a device that permits more than one different cell types to be physically separated within the culture dish environment, while the inner cellular surface is exposed to the simulated hemodynamic flow patterns.

2. Description of Related Art

Atherosclerosis is a vascular inflammatory disease characterized by lesion formation and luminal narrowing of the arteries. Endothelial cell (EC) and smooth muscle cell (SMC) regional phenotypes have significant implications in the progression of vascular disease. During early atherogenesis, the endothelium becomes activated, leading to increased adhesion molecule expression, permeability to lipoproteins and cytokine generation. Such environmental changes can influence SMCs to undergo "phenotypic switching" characterized by morphological changes, increased proliferation and migration, and decreased expression of defining quiescent SMC markers.

Atherosclerosis is further characterized by its focal development in large arteries at hemodynamically defined regions, such as at bifurcations that produce complex flow patterns. Atheroprone regions, susceptible to plaque formation, are subjected to low time-averaged shear stress and "disturbed" oscillatory flow patterns. In contrast, atheroprotective regions, which are less susceptible to plaque formation, are exposed to relatively higher time averaged shear stress and pulsatile laminar flow (13, 39). In regions of chronic disturbed flow, changes in EC phenotype, such as increased adhesion molecule expression, (i.e., vascular cell adhesion molecule 1 (VCAM-1), intercellular adhersion moldule 1 (ICAM-1), e-Selectin), and transendothelial permeability to low density lipoproteins (LDL), will effect the local signaling environment and can alter SMC phenotype, leading to proliferation, migration and the pathogenesis of atherosclerosis.

The factors controlling changes in SMC phenotype involving EC's and hemodynamic flow patterns are not fully understood. However, a hallmark of SMC phenotype switching in atherosclerosis is the suppression of contractile proteins that define the differentiated SMC, including SMMHC, SMαA, and myocardin.

To understand the role of shear stress on the endothelium in atherogenesis, in vitro models that expose ECs to a variety of shear stress conditions have been extensively studied. Since ECs can discriminate variations in flow patterns and are sensitive to both shear stress magnitude and time-varying features of hemodynamics, emulating in vivo flow environments appears to have a greater impression on recapitulating the in vivo phenotype of the endothelium. Additionally, few studies have shown the intricate interactions and cross-communications of ECs and SMCs in the presence of any type of flow, and no known studies to date have examined how in vivo-derived human hemodynamic forces on the endothelium regulate SMC phenotypic switching, as it is classically defined by the literature.

SUMMARY OF THE INVENTION

An aspect of the invention is, but not limited thereto, an in vitro biomechanical model used to apply hemodynamic (i.e., blood flow) patterns modeled after the human circulation to human/animal cells in culture. This model replicates hemodynamic flow patterns that are measured directly from the human circulation using non-invasive magnetic resonance imaging and translated to the motor that controls the rotation of the cone. The cone is submerged in fluid (i.e., cell culture media) and brought into close proximity to the surface of the cells that are grown on the plate surface. The rotation of the cone transduces momentum on the fluid and creates time-varying shear stresses on the plate or cellular surface. This model most closely mimics the physiological hemodynamic forces imparted on endothelial cells (cell lining blood vessels) in vivo and overcomes previous flow devices limited in applying more simplified nonphysiological flow patterns.

Another aspect of this invention is directed to incorporate a commercially available TRANSWELL (a coculture dish comprising an artificial porous membrane), for example a 75 mm-diameter TRANSWELL. This permits two, three, or more different cell types to be physically separated within the culture dish environment, while the inner cellular surface is exposed to the simulated hemodynamic flow patterns. Other significant modifications include in-flow and out-flow tubing to supply media, drugs, etc. separately and independently to both the inner and outer chambers of the coculture model. External components are used to control for physiological temperature and gas concentration. The physical separation of adherent cells by the artificial TRANSWELL membrane and the bottom of the Petri dish permits each cell layer, or surface, to be separately isolated for an array of biological analyses (i.e., protein, gene, etc.).

The directed use of this invention includes 1) to study the cross-talk between human/animal endothelial and smooth muscle cells—two critical cell types that comprise the blood vessel wall and involved in the pathological development of atherosclerosis (heart disease, stroke, peripheral vascular disease) and other vascular diseases. 2) This model may also be used as a diagnostic model in testing novel drug-based therapies for toxicity, inflammation (e.g. monocyte adhesion, inflammatory cytokine release, inflammatory gene induction) and permeability.

Some exemplary novel aspects of various embodiments related to this invention include, but not limited thereto, the following, in no specific order:

The device can replicate with the highest level of fidelity the hemodynamic shear stress profiles in the arterial circulation susceptible to and protective of atherosclerosis and from patients susceptible to other physiological (e.g., exercise) or pathological conditions (e.g., hypertension, diabetes, dyslipidemia).

The device can replicate with the highest level of fidelity any type of measurable or idealistic shear stress profiles from the arterial, venous, or any organ circulation.

Exposure of the hemodynamic flow patterns on the inner surface of a TRANSWELL membrane, with or without another cell type cultured on the opposing side of the membrane.

Exposure of the hemodynamic flow patterns on the inner surface of a TRANSWELL membrane, with or without another cell type cultured on the bottom surface of the TRANSWELL dish.

Exposure of the hemodynamic flow patterns on the inner surface of a TRANSWELL membrane, with or without another cell type cultured on the opposing side of the membrane and with or without a third cell type cultured on the bottom surface of the TRANSWELL dish. The third cell may include monocytes or macrophages for inflammatory cell adhesion assays.

Exposure of the hemodynamic flow patterns on the inner surface of a TRANSWELL membrane, with or without another cell type cultured on the opposing side of the membrane and with or without a third cell type in suspension in the media of the inner surface of the TRANSWELL membrane.

Clamps mount on the sides of the TRANSWELL used to hold in place the inflow and out-flow tubing for both the inner (upper) chamber and outer (lower) chamber. This is used to perfuse in and out media, biochemical compounds, agonists, antagonists, etc. of the upper and/or lower chamber of the TRANSWELL separately without disturbing the flow environment. Media extracted from the experiment can be used to further test cytokine or humoral factor secretion from either layer.

The ability to isolate each cell type independently (one, two, or three different cell types used) from a single experiment for post-processing biological (proteomic/genomic) analyses, including gene arrays, proteomics.

The device can accept and test any cell type from any species that is adherent or nonadherent.

The device can be used as a vascular biomimetic cell culture model for investigating all phases from embryonic vascular development to the severe cases of atherosclerosis in adults. For example, endothelial cells may be plated in the inner surface and/or smooth muscle cells plated on the opposing side of the TRANSWELL membrane and/or macrophages (or leukocytes) in the upper or lower chamber.

The device can be used to test the compatibility, cellular adhesion, and phenotypic modulation of cells from vascular stent material under hemodynamic conditions. For example, endothelial and/or smooth muscle cells may be seeded next to, on top of, or underneath the material, mounted on the stationary surface of the device. Materials include but are not limited to metallic nanoporous metals, polymers, biodegradable polymers, carbon surfaces, scratched or etched surfaces.

The device can be used to test drug (i.e., compound) elution from vascular stent material under hemodynamic conditions in the presence or absence of cells.

The device can be used to test the compatibility, cellular adhesion, and phenotypic modulation of cells seeded on or adjacent to surfaces coated with polymeric material under hemodynamic conditions.

The device can be used as a vascular biomimetic cell culture model for the investigation of the blood-brain barrier. For example, endothelial cells may be plated in the inner surface and/or glial cells and/or astrocytes and/or neurons plated on the opposing side of the TRANSWELL membrane and/or the bottom Petri dish surface.

The device can be used as an airway biomimetic cell culture model for the investigation of the development and progression of asthma. For example, epithelial cells may be plated in the inner surface and/or smooth muscle cells plated on the opposing side of the TRANSWELL membrane and/or macrophages (or leukocytes) in the lower chamber. Rhythmic breathing patterns are emulated by the movements of the cone in close approximation to secrete and/or artificial mucosal layer between the cone and epithelial surface.

The device can be used as renal biomimetic model for the investigation endothelial cell and epithelial podocyte interaction.

The device can be used to create a specific humoral environment that mimics patient drug therapy and then determine compatibility of a known or unknown drug compound in conjunction with the patient drug therapy. For example, the device can be run for a specific time with the drug LIPITOR (atorvastatin) in the media and then an unknown drug can be added to determine changes in toxicity, inflammation (e.g. monocyte adhesion, inflammatory cytokine release, inflammatory gene induction) and permeability.

The device can be used to determine functional changes in vascular cells or other organ cells types taken from patients with an identified genotype linked to drug toxicity or some pathophysiological endpoint. For example, endothelial cells from a patient with a single nucleotide polymorphism (SNP) identified to be associated with drug toxicity can be used to test novel or known compounds for changes in toxicity, inflammation (e.g. monocyte adhesion, inflammatory cytokine release, inflammatory gene induction) and permeability. This is commonly referred to as pharmacogenomics.

An embodiment of this invention is a method of applying hemodynamic patterns to cells in culture, said method comprising the steps of plating a first set of cells on a TRANSWELL, plating a second set of cells on said TRANSWELL, wherein said first set of cells are separated from said second set of cells, adding a fluid to said TRANSWELL; and causing rotation of said fluid for a period of time, wherein said medium thus exerts a shear force upon said second set of cells.

Another embodiment of this invention is a method of applying hemodynamic patterns to cells in culture, said method comprising the steps of monitoring the hemodynamic pattern of a subject; modeling said hemodynamic pattern into a set of electronic instructions; and using a device to cause a shear stress on a plurality of sets of cells on a TRANSWELL based upon said electronic instructions.

Another embodiment of this invention is a hemodynamic flow device, comprising an electronic controller; a motor, wherein said motor is operated via said electronic controller; a cone connected to said motor, whereby said cone is rotated by said motor; a TRANSWELL with a membrane, wherein said cone is at least partially submerged in a medium in said TRANSWELL and wherein said cone exerts a rotational force upon said medium; an inlet flow tube to add media to said TRANSWELL; and an outlet flow tube to withdraw media from said TRANSWELL.

DETAILED DESCRIPTION OF THE INVENTION

Atherosclerosis

Figure 1:
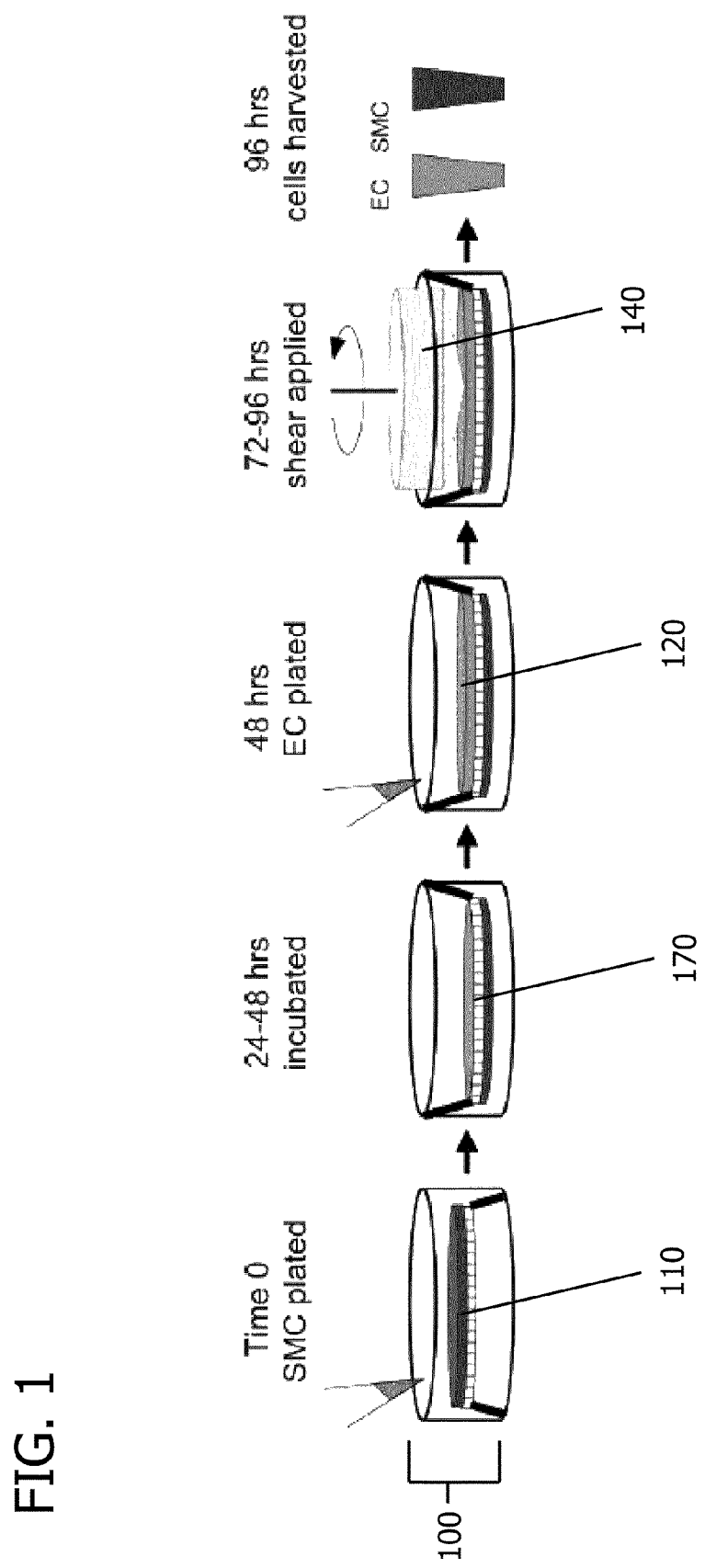
FIG. 1 provides an exemplary view of EC/SMC plating on a TRANSWELL.

Atherosclerosis preferentially develops at arterial regions, such as bifurcations and regions of high curvature, characterized by disturbed, low time averaged and oscillatory wall shear stress. Atheroprone regions in vivo and atheroprone shear stress on the endothelium in vitro can induce proinflammatory priming indicated by the activation and regulation of downstream inflammatory targets. Although ECs and SMCs are two major cell types known to undergo phenotypic modulation, or "switching," during initiating atherosclerotic events, until this invention it was unknown whether hemodynamic forces on ECs regulated or contributed to this process in SMCs. Human-derived atheroprone shear stresses applied to ECs modulate a proinflammatory phenotype in ECs and SMCs and proatherogenic phenotypic switching in SMCs via epigenetic modifications at the chromatin level. This is a process referred to as mechanotranscriptional coupling.

Results from the present coculture process support the hypothesis that hemodynamics induce vascular EC and SMC priming toward a proatherogenic response, thus validating the use of the coculture system as a new physiologically relevant biomimetic vascular model for the study of early atherosclerotic events. These results are consistent with previously published atherosclerosis-related in vivo and in vitro flow studies (see FIG. 10). Moreover, previous TRAN-SWELL coculture models of ECs and SMCs have been restricted to static type experiments, with the exception of a few flow studies, and no known studies have employed physiologically relevant, human-derived hemodynamic flow patterns. The present process overcomes these limitations by directly comparing two hemodynamic flow patterns, yielding a more physiologically relevant model for accurately comparing in vivo regions in the vasculature, and focused on classic SMC differentiation markers.

A hallmark of SMC phenotypic modulation in vascular disease is altered expression of genes that define the contractile phenotype. SMC differentiation markers and transcription factors that are delineators of a differentiated SMC are affected by atheroprone flow. The loss of expression of differentiation markers (SMαA and myocardin) and induction of the inflammatory marker VCAM-1 at both mRNA and protein levels confirmed that ECs exposed to atheroprone flow differentially regulate the SMC phenotype compared with atheroprotective flow. ChIP analysis revealed that the mechanism initiating atheroprone-induced loss of CArG-dependent SMC gene expression involved reduction of SRF binding to CArG box regions of SMαA and SMMHC and deacetylation of histone H4 compared with atheroprotective flow. This was not the case for the early growth response gene c-fos. These results are consistent with a monoculture SMC study in response to PDGF-BB treatment and, most importantly, the epigenetic fingerprint for SMαA, SMMHC, and c-fos in intact blood vessels in response to acute vascular injury. Thus, the general paradigm that histone H4 acetylation is critical for maintaining CArG chromatin promoter regions in a SRF-accessible state is differentially regulated by two distinct hemodynamic flow patterns exposed to ECs. The SRF coactivator myocardin plays a critical role in forming a higher-order complex with SRF for the positive regulation SMC selective CArG-dependent genes. In contrast, KLF4 can abrogate myocardin-dependent regulation of CArG-dependent SMC differentiation genes. Myocardin expression was significantly reduced in response to atheroprone flow, whereas KLF4 tended to have increased expression. Since KLF4 gene expression can be rapidly and transiently induced in response to PDGF-BB in cultured SMCs and transiently induced in intact vessels following acute vascular injury up to six hours and returning to baseline by twenty-four hours, it is possible that the maximal and most significant changes in KLF4 expression were not captured at this time point. Nevertheless, gene profiles generated in this study correlate with existing data from the literature, and, taken together, the results suggest that phenotypic modulation of SMCs exposed to atheroprone flow occurs at the transcriptional level and involves the well-characterized SRF/myocardin and KLF4 signaling axis.

Of interest, ECs exhibited reduced KLF4 expression in atheroprone flow. KLF4 has been shown to be regulated by flow in ECs in monoculture; however, it was previously not known that KLF4 is differentially expressed by atheroprone flow compared with atheroprotective flow. The functional significance of KLF4 in ECs has recently been shown to be similar to that of KLF2 (i.e., anti-inflammatory, atheroprotective, and hemostasis control). Moreover, KLF4 has been implicated in cell cycle regulation, and greater cell cycle activity has been reported for atheroprone relevant flow in vitro and regions in vivo. Thus, the regulation of KLF4 transcription may serve an equally vital role in regulating vascular EC and SMC proliferation. Furthermore, while myocardin has been shown to decrease with acute, mechanical vascular injury and KLF4 increases, this process provides evidence that these transcription factors are differentially regulated in a model that mimics early atherogenic events. Regulation in vivo in atherosclerosis is currently unknown.

Figure 10:
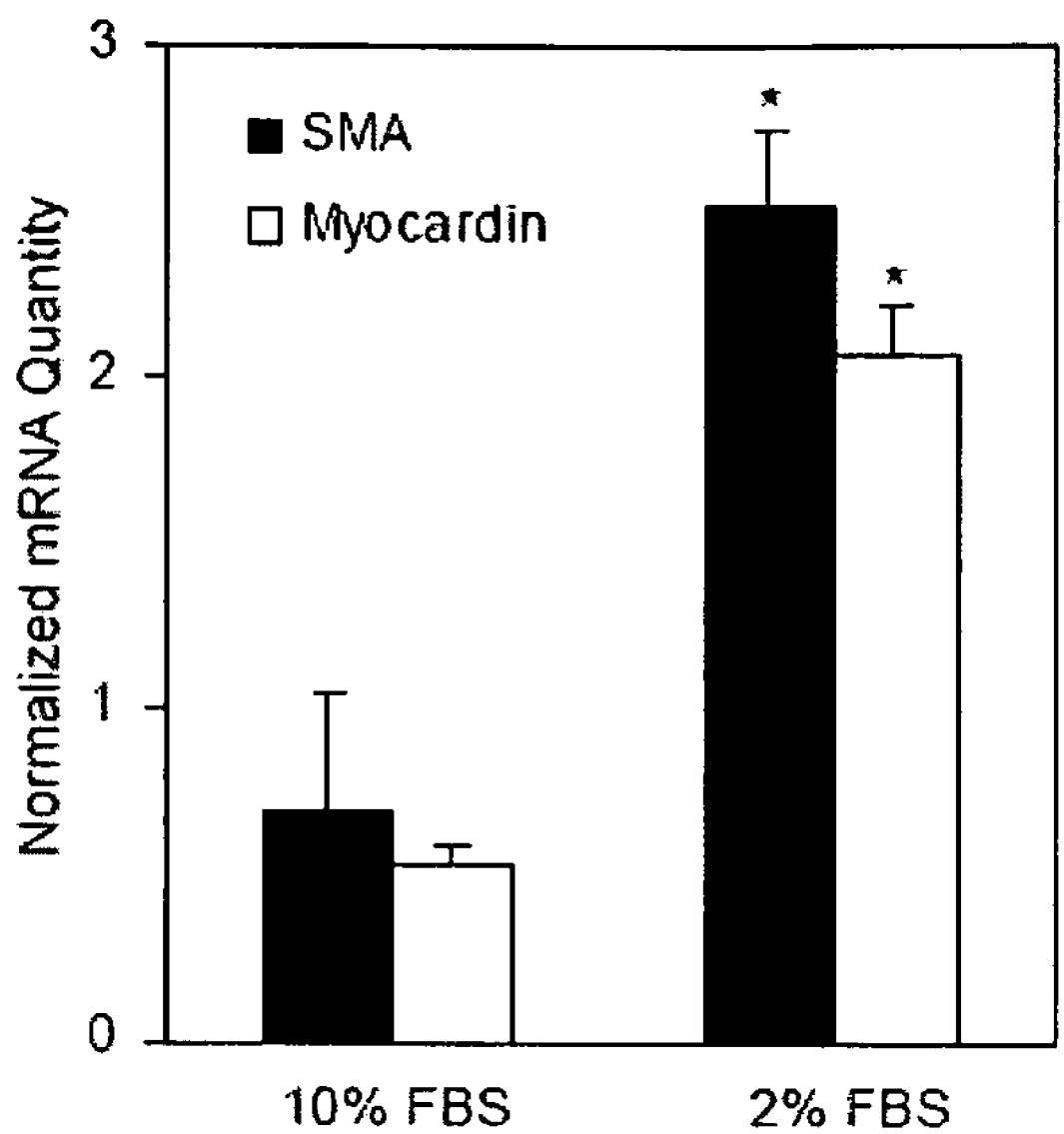
FIG. 10 shows an exemplary graph demonstrating normalized gene expression.

Surprisingly, SMMHC was the only SMC marker that did not follow the expected modulation trends. This may be due to RT-PCR primer recognition of both SMMHC isoforms (SM-1 and SM-2). Analysis of each isoform separately may elucidate a response consistent with the other SMC markers. Analysis at later time points (i.e., forty-eight hours) may resolve this. The combined phenotypic responses of both ECs and SMCs in the presence of atheroprone flow are strikingly similar to historical EC and SMC phenotype profiles defined in human and experimental models of atherosclerosis (FIG. 10).

Evaluation of EC gene expression in response to atheroprone relative to atheroprotective flow is consistent with the only EC monoculture study using similar flow profiles as well as studies using similar magnitudes of steady shear stress and in vivo models of atherosclerosis, emphasizing that hemodynamics more robustly regulate the EC phenotype than the presence of SMCs. ECs exposed to twenty-four hours of atheroprone flow induced higher levels of proatherogenic and proliferative genes and proteins for IL-8, VCAM-1, and PCNA commensurate with reductions in eNOS, Tie2, and KLF2. The expression loss of eNOS and Tie2 suggests higher rates of remodeling and increased permeability, characteristic features of atherosusceptible regions in vivo. Evidence has established the role of KLF2, and possibly KLF4, as an upstream transcriptional regulator of atheroprotection. Atheroprotective hemodynamics in vitro and regions in vivo appear to be a key modulator of KLF2 expression and transcriptional control. SMCs also exhibited an early inflammatory response to atheroprone flow, as indicated by increased VCAM-1 mRNA levels. VCAM-1 modulation has been observed in SMCs of human atherosclerotic plaques and has been linked to proliferation during early atherogenesis in vitro and in vivo. However, since the proliferative marker PCNA showed no change in SMCs for atheroprone flow, it is possible that a more migratory SMC phenotype is present in this system.

The EC-secreted cytokine(s)/mitogen(s) that regulates SMC phenotypic modulation during early atherogenesis has yet to be elucidated and includes candidates such as PDGF-BB, IL-1, and IL-8. Here, we show ECs increase IL-8 mRNA production and IL-8 secretion following atheroprone flow. Indeed, IL-8 can stimulate the induction of a migratory phenotype in SMCs. Therefore, IL-8 secretion by ECs may be one mechanism by which SMCs regulate a more synthetic phenotype. Of interest, a recent study in apolipoprotein $E^{-/-}$ mice showed that experimentally induced low shear stress resulted in an increase in growth-related protein (Gro)-α mRNA. However, given the in vivo nature of this study, it was not determined whether changes in Gro-α mRNA were in ECs, SMCs, or both. Although Gro-α binds the same receptors as IL-8, no murine homolog of IL-8 exists. The human coculture model is therefore ideal for examining the role of EC-derived IL-8 on SMCs, and future studies are ongoing to establish the relative contributions of such cross-communication mechanisms.

Cell morphology changes observed in atheroprone versus atheroprotective flow were also signs of early remodeling that could lead to localized downstream atherogenic responses. ECs are known to reorient in the direction of flow under pulsatile physiologic conditions and maintain a more polygonal shape after exposure to disturbed flow, as observed in our system. However, our understanding of SMC reorientation due to shear stress sensed by the endothelium is in its earliest stages. SMCs orient more perpendicular to hemodynamic flow under the atheroprotective waveform, whereas SMCs exposed to atheroprone flow resulted in more random alignment. Importantly, this SMC orientation is nearly identical to the spatial patterning of SMCs in an intact blood vessel at bifurcating regions, regions highly susceptible to atherosclerosis. Together, this suggests that hemodynamic flow can regulate both EC and SMC orientation by unique control mechanisms inherent to distinct atheroprone or atheroprotective flow patterns.

This invention presents a novel in vitro coculture model using human ECs and SMCs that shows that human hemodynamic forces, atheroprotective or atheroprone, applied directly to the endothelium can modulate the SMC phenotype and influence SMC remodeling, a process we defined as mechanotranscriptional coupling. Moreover, the snapshot of phenotypic and morphologic alterations in ECs and SMCs indicates that hemodynamic forces on the endothelium are an important modulator of atherogenesis.

As shown in FIG. 1, a TRANSWELL 100 is used in the hemodynamic flow process. The TRANSWELL allows multiple cells 110, 120 to be tested in parallel and also provides a porous interface. An exemplary process for plating to coculture is also shown; however, this process may be altered by processes available to one skilled in the art. In this embodiment, SMCs 110 are plated at an initial time, after which the TRANSWELL is inverted. The SMCs 110 are incubated for twenty-four to forty-eight hours, after which ECs 120 are plated on the TRANSWELL and incubated. The bottom of the Petri dish into which the TRANSWELL is inserted may also serve as a third surface to plate an additional cell type or the same cell type as ones plated directly on the TRANSWELL membrane 170. After the ECs 120 are incubated, the cone 140 of the motor and cone device is used to apply a shear force.

Figure 2:
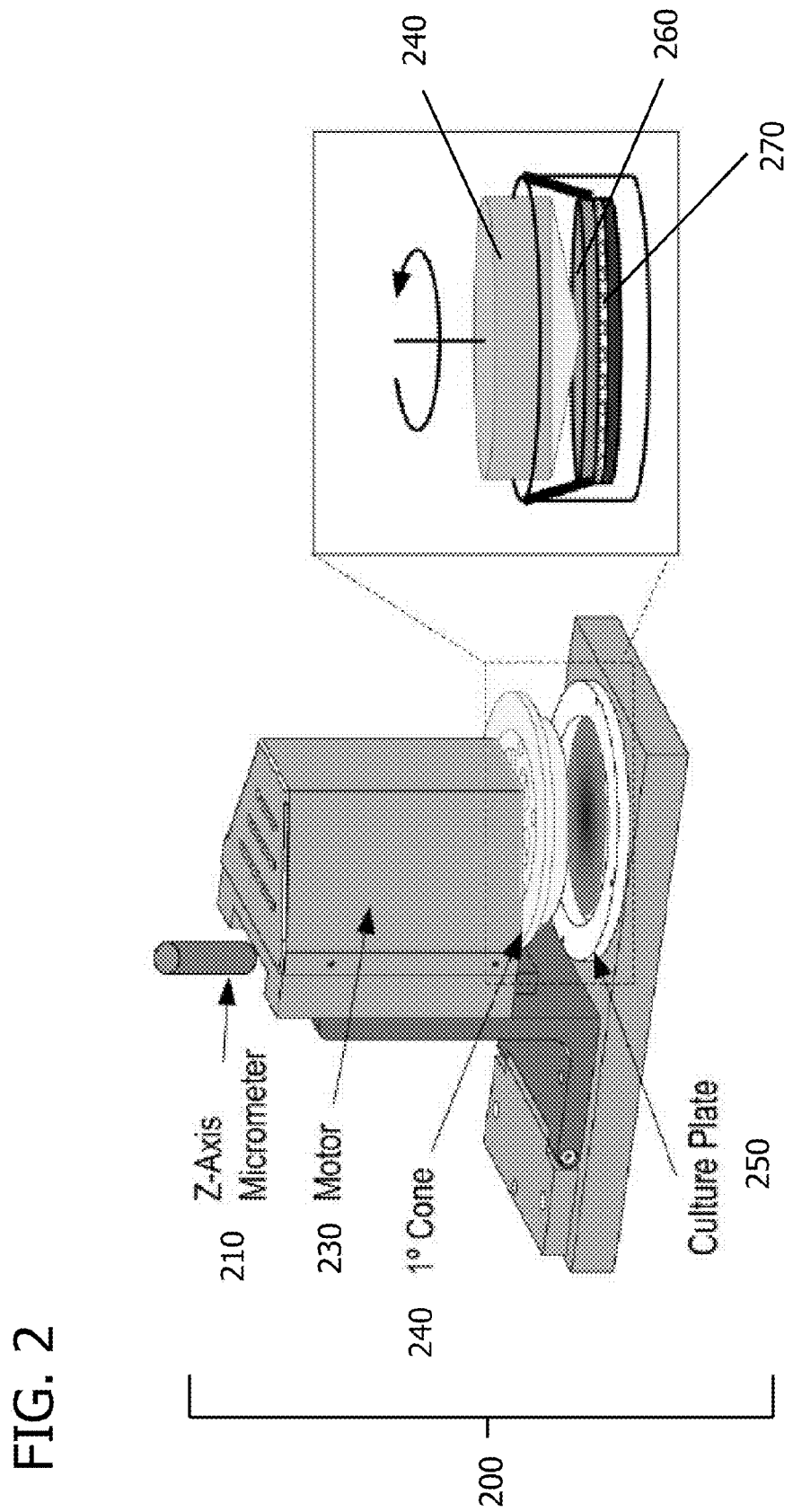
FIG. 2 provides a view of the cone and plate flow device, modified to accommodate a TRANSWELL culture dish.

As shown in FIG. 2, a motor and cone device 200 is used to apply the shear forces upon the cells. A motor 230 causes the cone 240 to rotate at a precise rotational velocity, and can effect the rotation in either direction (i.e. clockwise or counterclockwise). This rotational force is applied to a liquid medium by the cone. In turn, this medium applies shear forces directly to the cells 260 on the TRANSWELL membrane 270 in the culture plate 250. Software is programmed to control the continuous motion of the cone. This software file is uploaded to a motor controller unit, and the information is then sent directly to the motor to perform the programmed task.

In a preferred embodiment, the medium is a cell culture broth that is formulated to sustain the integrity and health of the cells during the experiment. The formulation is not limited and may vary depending on the cell types being use and experimental study. Additionally, drug compounds may be a part of this formulation either initially, or perfused into the cell culture environment during the course of a flow experiment. This may include, but is not limited to compound that can inhibit, activate or alter the function of proteins/genes in the cells.

In one embodiment, the device can be used to test the compatibility, cellular adhesion, and phenotypic modulation of cells from vascular stent material under hemodynamic conditions. For example endothelial and/or smooth muscle cells may be seeded next to, on top of, or underneath the material, mounted on the stationary surface of the device. Materials include but are not limited to metallic nanoporous metals, polymers, biodegradable polymers, carbon surfaces, scratched or etched surfaces. These materials further include non-degradable polymer or co-polymer, such as polyethylene-co-vinyl acetate (PEVA) and poly n-butyl methacrylate, and can be coated onto the TRANSWELL surface. These materials further include biodegradable polymer or co-polymer, such as polylactic acid glycolic acid (PLGA) or phosphorylcholine, and can be coated onto the TRANSWELL surface. These materials further include nanoporous surface modification, such as a ceramic, metal or other material and can be added to the TRANSWELL surface as a nanoporous surface modification. These materials further include microporous surface modification, such as a ceramic, metal, physical etching (such as sand blasting) or other material added to the TRANSWELL surface to form a microporous surface modification.

In another embodiment of this invention, the device can operate with cells plated on either one or both sides of the TRANSWELL membrane. The membrane portion of the TRANSWELL membrane can comprise any biological or synthetic material, with a range of porosities and thicknesses. Similarly, the structure that holds and supports the TRANSWELL membrane can be made of any synthetic material.

EXAMPLE

The following is an example of a method of using the present invention, and is not intended to limit the scope of the invention to the exact method described in this example.

Human Cell Isolation and Culture.

Primary human ECs and SMCs were isolated from umbilical cords, expanded, and used as cell sources. Human ECs were isolated from the umbilical vein (human umbilical vein ECs) as previously described, followed by isolation of SMCs from the vein using a similar method as previously described.

ECs were used for experimentation at passage 2 and SMCs were for experimentation used up to passage 10, both of which have been established to retain the basal EC/SMC phenotype based on the retention of specific EC and SMC markers. Cell types were separately cultured and passaged using medium 199 (M199; BioWhitaker) supplemented with 10% FBS (GIBCO), 2 mM L-glutamine (BioWhitaker), growth factors [10 µg/ml heparin, (Sigma), 5 µg/ml endothelial cell growth supplement (Sigma), and 100 U/ml penicillin-streptomycin (GIBCO)].

TRANSWELL coculture plating conditions.

As shown in FIG. 1, porous TRANSWELL membranes (polycarbonate, 10 pm thickness and 0.4 pm pore diameter, no. 3419, Corning) were initially coated with 0.1% gelatin on the top and bottom surfaces. The TRANSWELL was inverted, and SMCs were plated at a density of 10,000 cells/cm$^2$ on the bottom surface for 2 h. The TRANSWELL was then turned back over into the holding well for forty-eight hours in reduced serum growth medium (M199 supplemented with 2% FBS, 2 mM L-glutamine, and 100 U/ml penicillin-streptomycin). ECs were then plated on the top surface of the membrane at a density of 80,000 cells/cm$^2$ under the same media conditions for an additional twenty-four hours. For hemodynamic flow experiments, two dishes were prepared in parallel.

Coculture Hemodynamicflow Device and Flow Patterns.

As shown in FIG. 2, the novel coculture in vitro model of this process uses arterial flow patterns modeled from the human circulation were applied to human ECs. A version of the cone and plate device is a direct drive, whereby the cone is directly driven by the motor (rather than off to one side through a timing belt connection). This model was modified to incorporate a 75-mm-diameter TRANSWELL dish (polycarbonate, 10 pm thickness and 0.4 pm pore diameter, Corning). Additional modifications included a base to securely hold the TRANSWELL dish, a smaller cone (71.4 mm diameter and 1° cone angle) to fit inside the TRANSWELL compartment, and special mounting brackets for in-flow and out-flow tubing for both the inner and outer chambers of the TRANSWELL, which provides direct access to the culture fluid environment to continuously exchange media to both EC and SMC layers. Through the rotation of the cone, the system imposes hemodynamic shear stress on the EC layer of the EC/SMC coculture.

Figure 3:
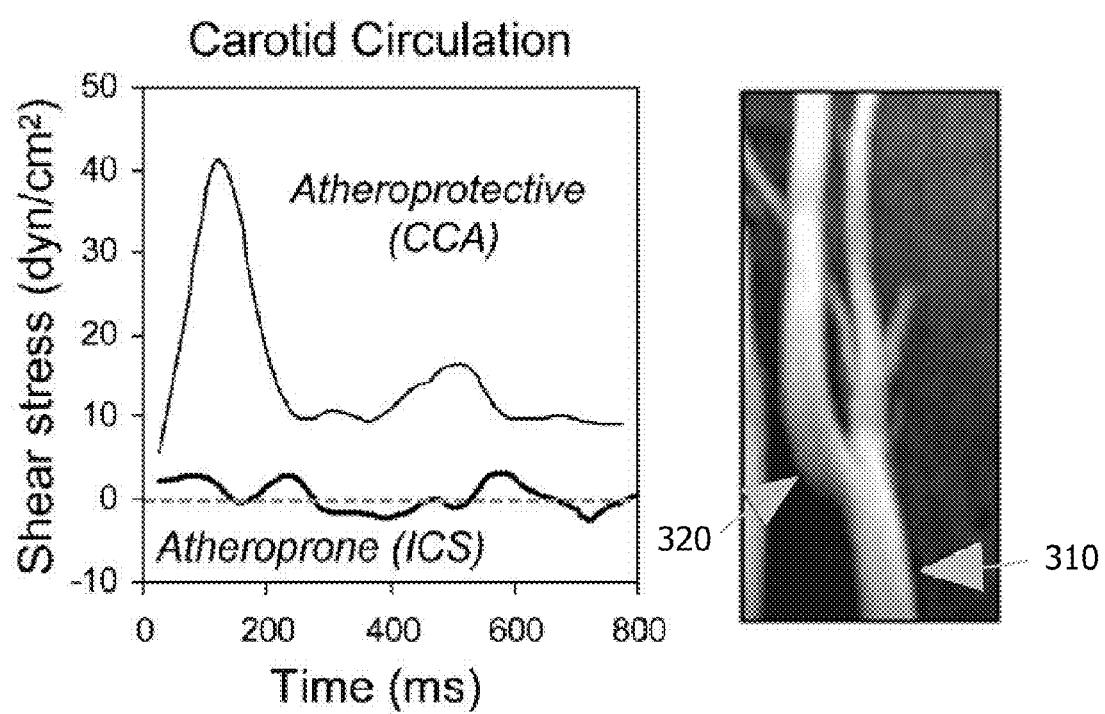
FIG. 3 provides a graph displaying an exemplary hemodynamic flow pattern derived from an MRI of a the human common carotid artery (CCA) and internal carotid sinus (ICS). Also shown is such an exemplary MRI.

Hemodynamic flow patterns used in this process were derived from MRI of the human common carotid artery (CCA) and internal carotid sinus (ICS) to best simulate atheroprotective (CCA) and atheroprone (ICS) shear stress patterns in vitro, respectively. The two hemodynamic flow conditions were run in parallel for each EC/SMC subpopulation. FIG. 3 shows human hemodynamic flow profiles (left) from the common carotid (CCA; atheroprotective, right, 310) and internal carotid sinus (ICS; atheroprone, 320) were imposed on the EC surface of the TRANSWELL.

Real-Time RT-PCR.

After the application of hemodynamic flow patterns for twenty-four hours, SMCs and ECs were rinsed two times in PBS with $Ca^{2+}/Mg^{2+}$. The membrane was removed from the holding dish and inverted. SMCs were gently scraped toward the center of the dish with small flexible cell scrapers. Cells were then rinsed onto a sterile surface using 1 ml PBS, which was then transferred to a microcentrifuge tube on ice. The membrane was turned over and placed flat on a sterile surface, and ECs were scraped in 1 ml PBS and then transferred to a separate microcentrifuge tube on ice. Tubes were centrifuged, and PBS was removed. Total RNA was extracted using TRIZOL reagent (Invitrogen) (a monophasic solution of phenol and guanidine isothiocyanate) and reverse transcribed using the ISCRIPT cDNA Synthesis Kit (Bio-Rad). Primers were designed using BEACON DESIGNER 2.0 (primer design software) for smooth muscle α-actin (SMαA), myocardin, smooth muscle myosin heavy chain (SMMHC), VCAM-1, monocyte chemoattractant protein-1 (MCP-1), endothelial nitric oxide synthase (eNOS), angiopoiten receptor Tie2, IL-8, and Kruppel-like transcription factors (KLF2 and KLF4). Table 1 shows sense and antisense primers used for each human gene. The expression of mRNA was analyzed via real-time RT-PCR using AMPLITAQ GOLD (a modified Taq DNA polymerase that is activated when the reaction reaches an optimal annealing temperature) (Applied Biosystems), SYBR GREEN (a specific double-stranded DNA binding dye used to detect PCR product as it accumulates during PCR cycles) (Invitrogen), and an ICYCLER (a real-time PCR detection system) (Bio-Rad).

TABLE 1

RT-PCR primers designed for gene and ChIP analyses

| | Sense Primer (SEQ ID NO.) | Antisense Primer |
|---|---|---|
| Real-time RT-PCR primers | | |
| $β_2$-Microglobulin | 5'-AGCATTCGGGCCGAGATGTCT-3' (1) | 5'-CTGCTGGATGACGTGAGTAAACCT-3' (15) |
| eNOS | 5'-CTCCATTAAGAGGAGCGGCTC-3' (2) | 5'-CTAAGCTGGTAGGTGCCTGTG-3' (16) |

TABLE 1-continued

RT-PCR primers designed for gene and ChIP analyses

| | Sense Primer (SEQ ID NO.) | Antisense Primer |
|---|---|---|
| IL-8 | 5'-CATGACTTCCAAGCTGGCCG-3' (3) | 5'-TTTATGAATTCTCAGCCCTC-3' (17) |
| KLF2 | 5'-GCACCGCCACTCACACCTG-3' (4) | 5'-CCGCAGCCGTCCCAGTTG-3' (18) |
| KLF4 | 5'-GGCCAGAATTGGACCCGGTGTAC-3' (5) | 5'-GCTGCCTTTGCTGACGCTGATGA-3' (19) |
| MCP-1 | 5'-CCAGCAGCAAGTGTCCCAAAG-3' (6) | 5'-TGCTTGTCCAGGTGGTCCATG-3' (20) |
| Myocardin | 5'-TGCAGCTCCAAATCCTCAGC-3' (7) | 5'-TCAGTGGCGTTGAAGAAGAGTT-3' (21) |
| SMαA | 5'-CACTGTCAGGAATCCTGTGA-3' (8) | 5'-CAAAGCCGGCCTTACAGA-3' (22) |
| SMMHC | 5'-AGATGGTTCTGAGGAGGAAACG-3' (9) | 5'-AAAACTGTAGAAAGTTGCTTATTCACT-3' (23) |
| Tle2 | 5'-CCGTTAATCACTATGAGGCTTGGC-3' (10) | 5'-GTGAAGCGTCTCACAGGTCCA-3' (24) |
| VCAM-1 | 5'-GTTTGTCAGGCTAAGTTACATATTGATGA-3' (11) | 5'-GGGCAACATTGACATAAAGTGTTT-3' (25) |
| ChIP analysis primers | | |
| SMαA, 5'-CArG | 5'-AGCAGAACAGAGGAATGCAGTGGAAGAGAC-3' (12) | 5'-CCTCCCACTCGCCTCCCAAACAAGGAGC-3' (26) |
| SMMHC. 5'-CArG | 5'-CTGCGCGGGACCATATTTAGTCAGGGGGAG-3' (13) | 5'-CTGGGCGGGAGACAACCCAAAAAGGCCAGG-3' (27) |
| c-fos | 5'-CCCGCACTGCACCCTCGGTG-3' (14) | 5'-TACAGGGAAAGGCCGTGGAAACCTG-3' (28) |

ChIP. chromatin immunoprecipitation; eNOS, endothelial nitric oxide synthase; KLF, Kruppel-like factor. MCP, monocyte chemoattractant protein: SMαA, smooth muscle α-actin: SMMHC, smooth muscle myosin heavy chain; CArG, CC(A/T)$_6$GG.

Western Blot Analysis.

Vascular SMCs and ECs were collected as described in Real-time PCR and lysed in RIPA buffer (1% Nonidet P-40, Na-deoxycholate, 1 mM EDTA, 1 mM PMSF, 1 mM Na3V4, 1 mM NaF, 1 μg/ml aprotinin, 1 μg/l leupeptin, and 1 pg/ml pepstatin). Total protein lysates were resolved on a 7.5% SDS-PAGE gel and blotted on a polyvinyl derivative membrane. Primary antibodies [SMαA (Sigma, 1:1,000), eNOS (BD Transduction Laboratories, 0.1 pg/ml), VCAM-1 (R&D Systems, 1:500), and PCNA (Cell Signaling, 1:1,000)] were incubated with the blot for one hour at room temperature or overnight at 4° C. Horseradish peroxidase-conjugated secondary antibodies [goat anti-rabbit, goat anti-mouse (Santa Cruz Biotechnology, 1:5,000), and donkey anti-goat (1:5, 000)] were incubated with the blot for one hour at room temperature. An ALPHAIMAGER 8900 (a gel imaging system) and ALPHAEASEFC software (image analysis software) were used for acquisition of blot image and densitometry analysis, respectively.

ELISA.

Cocultured TRANSWELLS were prepared and exposed to differential hemodynamic environments. Media perfused throughout the flow experiment were collected on ice after 4, 8, 12, and 24 h for each chamber of the membrane (i.e., EC- and SMC-conditioned media from atheroprone and atheroprotective flows). Samples were then stored at −80° C. until they were assayed for IL-8 secreted protein via ELISA (GE Healthcare). The concentration of protein was determined using a spectrophotometer at 450 nm and normalized to the volume of media collected per hour.

Chromatin Immunoprecipitation Assay.

After the application of flow patterns, chromatin immunoprecipitation (ChIP) was performed as previously described with modifications allowing for a quantitative analysis of protein:DNA interactions. Outflow media from each experiment were supplemented with 1% formaldehyde and then incubated with cells for 10 min immediately following 24 h of flow. Antibodies included rabbit polyclonal anti-serum response factor (SRF; Santa Cruz Biotechnology, 5 μg/ml) and anti-histone H4 acetylation (Upstate Biotechnologies, 5 μg/ml). Recovered DNA was quantified by fluorescence with PICOGREEN reagent (a fluorescent nucleic acid stain for quantifying double-stranded DNA) (Molecular Probes) according to the manufacturer's recommendations. Real-time PCR was performed on 1 ng genomic DNA from ChIP experiments with minor modifications as previously described. Real-time PCR primers were designed to flank the 5'-CC(a/T)$_6$GG (CArG) elements of SMaA, SMMHC, c-fos CArG. Table 1 shows the primers used for ChIP analysis. Quantification of protein:DNA interaction/enrichment was determined by the following equation: $2(C_{t\ Ref} - C_{t\ IP}) - 2(C_{t\ Ref\ No\ antibody\ control})$, where $C_{t\ Ref}$ is the reference threshold cycle $(C_t)$ and $C_{t\ IP}$ is the $C_t$ of the immunoprecipitate. ChIP data are representative of five to six independent experiments pooled together and analyzed in duplicate.

Immunofluorescence.

For immunofluorescence (IF), TRANSWELL membranes were fixed in 4% paraformaldehyde for both en face preparations and transverse sections. En face preparations were permeabilized in 0.2% Triton X-100. Primary antibody for SMCs was pipetted onto a piece of PARAFILM (self-sealing, moldable and flexible film) [Cy3-SMαA (Sigma, 4 μg/ml) and SMMHC (Biomedical Technologies, 1:100)], and the sample well was placed on top. Primary antibody for ECs [vascular endothelial cadherin (VE-cad; Santa Cruz Biotechnology, 2 μg/ml)] was then added directly to the inside of the well, and both antibodies were simultaneously incubated for one hour. Similarly, secondary antibodies [Cy2 donkey anti-goat (Jackson ImmunoResearch, 4 µg/ml) and ALEXA FLUOR 546 (a fluorescent dye with an orange emission color) goat anti-rabbit (Molecular Probes, 6 µg/ml)] were added to samples as required and incubated for 1 h. Samples were mounted by adding PROLONG GOLD Antifade Reagent (an antifade reagent) with 4',6-diamidino-2 phenylindole (DAPI; Molecular Probes) to a large coverslip and dropping the well on top. Another drop of DAPI was added to the inside of the well, and a 22-mm-diameter coverslip was placed on top and allowed to solidify. The holding well was removed from the mounted samples using a scalpel to allow for imaging. Confocal microscopy was used to image en face samples through the z-axis from the EC to SMC layer (Nikon ECLIPSE Microscope TE2000-E2 and Melles Griot Argon Ion Laser System no. 35-IMA-840).

To prepare the transverse sections, EC/SMC cultures were stained with phalloidin-488 (Molecular Probes) or FM 4-64FX (Molecular Probes) using the methodology described above, immersed in 30% sucrose overnight, frozen in OCT compound, sliced into 5-µm-thick sections with a cryostat, and then mounted for assessment by confocal microscopy. IF stained samples were analyzed using a confocal microscope and differential interference contrast for cell-to-cell interactions within the pores of the TRANSWELL membrane under static conditions, as previously described.

EC/SMC Orientation and Morphometric Measurements.

The orientation of ECs and SMCs relative to the direction of flow was quantified using confocal microscopy of IF stained samples. Following hemodynamic flow, the coculture was fixed as described above, and isosceles triangular samples from the 75-mm-diameter dishes were cut with the apex of the triangle pointing toward the center of the dish. This method established the correct orientation relative to the direction of flow. Samples were then stained as described above and mounted between two coverslips. For imaging, samples were oriented on the confocal stage with the triangle apex facing to the right, so that the direction of flow was consistent across all samples. Images were taken of ECs and SMCs in the same location, separated only by the membrane distance.

At least three microscopy fields were acquired over three independent experiments. METAMORPH software (i.e., image acquisition and analysis software) was used to determine the angle of orientation and shape factor (SF) for each cell analyzed relative to the direction of flow. To determine the elongation of cell types, borders stained for VE-cad (FIG. 6) and p-catenin (not shown) of ECs (CCA: n=111 and ICS: n=53) and SMαA (FIG. 6), SMMHC, and p-catenin (not shown) of SMCs (CCA: n=64 and ICS: n=25) were outlined, and measurements of the area and perimeter were outputted. SF was calculated using the following equation: $SF=(4\pi A)/P^2$, where A is the cell area and P is the perimeter. For each SF bin in the histogram range, the number of cells per bin was normalized to the total number of cells analyzed over the whole range to yield a normalized frequency. Histograms were plotted to show the distribution of SFs for each condition (see FIG. 7). For the angle of orientation, lines were drawn in both the direction of flow and along the long axis of the SMCs from both flow patterns (CCA: n=119 and ICS: n=104) and ECs for atheroprotective flow only (CCA: n=124). The angle between the two lines was measured as the orientation angle relative to the flow direction, and histograms were plotted so that the frequency of cells having the same orientation was represented as the bar length.

Data Analysis and Statistics.

Real-time RT-PCR results are reported as the fold induction of cycle amplification times for atheroprone flow samples compared with atheroprotective flow and normalized to endogenously expressed gene $\beta_2$-microglobulin. Student's t-test was conducted for mRNA, orientation, and elongation data to determine the significance in expression level or morphological changes as a function of hemodynamic flow pattern and time. Data from at least three independent experiments per condition were used for analysis and evaluated at $P<0.05$.

EXEMPLARY RESULTS

Optimization of EC/SMC Coculture Plating and Growth Conditions.

Figure 4:
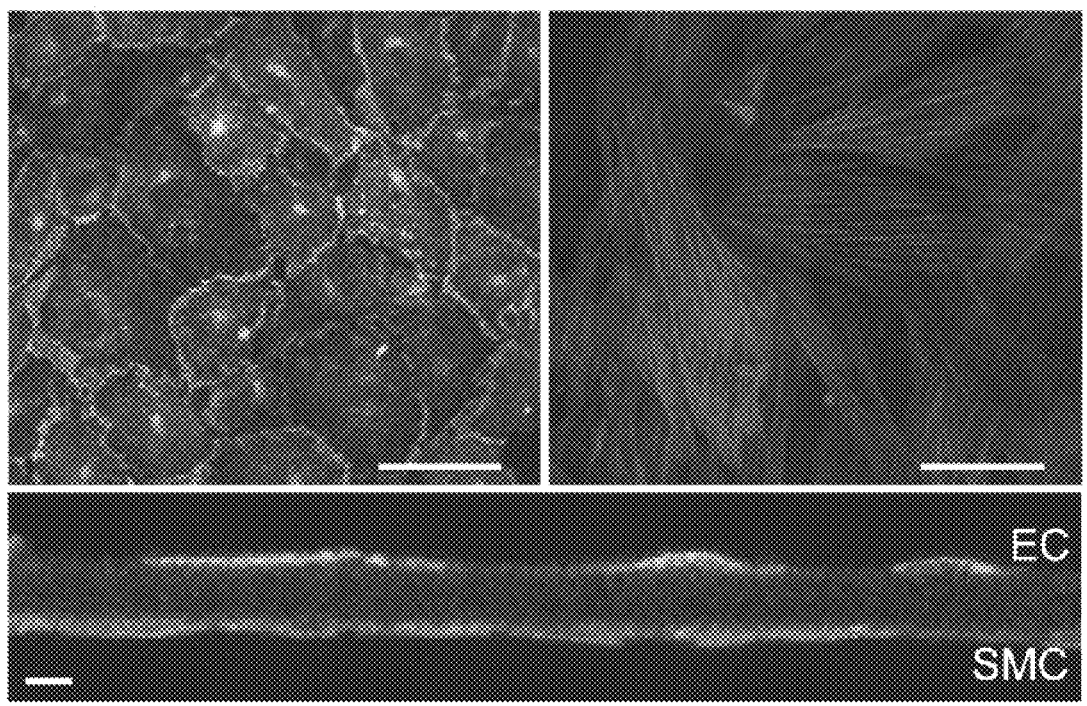
FIG. 4 shows exemplary confluent layers of ECs and SMCs twenty-four hours following EC seeding.

Coculture conditions for human EC and SMC plating were optimized so that each cell type reached confluence prior to the application of hemodynamic flow. FIG. 4 shows confluent layers of ECs and SMCs twenty-four hours following EC seeding. More specifically, FIG. 4 shows ECs (left) and SMCs (right) cocultured for twenty-four hours showing confluency status (Top, en face images; bottom, transverse section). ECs retained their classic polygonal morphology, forming adherens junctions, as demonstrated by the continuous peripheral staining of VE-cad, whereas SMCs were elongated and randomly oriented in the typical "hill and valley" formation. In SMCs plated alone, reduced serum media (2% FBS compared with 10% FBS) increased the mRNA expression of SMC markers SMαA and myocardin, indicating a more differentiated SMC phenotype (normalized gene expression with 2% FBS: SMA, 2.51±0.36 and myocardin, 2.07±0.05; with 10% FBS: SMA, 0.69±0.23 and myocardin, 0.54±0.14; see FIG. 10).

Figure 5:
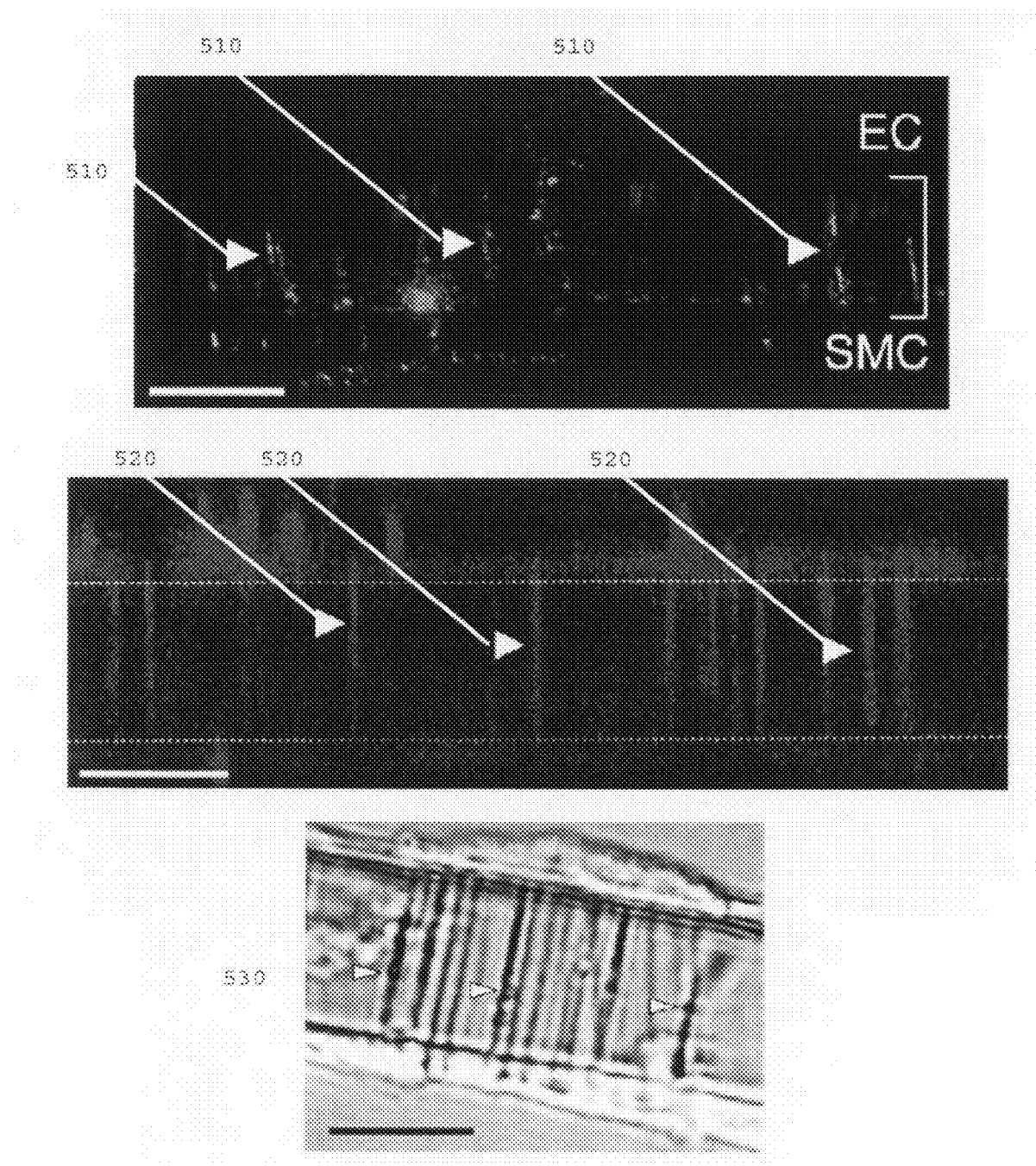
FIG. 5 shows exemplary transverse sections stained for F-actin and FM 4-64 or visualized by differential interference contrast showing cellular processes within membrane pores.

A murine coculture model has recently demonstrated that ECs and SMCs physically interact and communicate via gap junctions through linear pores of the TRANSWELL membrane. This model emulates myoendothelial junctions present within the vascular wall in vivo, creating a means for ionic communication via gap junctions and physical heterocellular adhesion. To determine whether EC/SMC physical interactions are formed in our human coculture model, transverse sections of the TRANSWELL membrane were IF labeled for F-actin or FM 4-64FX and analyzed using confocal and phase contrast microscopy. The results shown in FIG. 5 demonstrate that cellular processes are present in the pores, establishing heterocellular interactions. Transverse sections are stained for F-actin (top) and FM 4-64 (middle) or visualized by differential interference contrast (bottom) and showed cellular processes within membrane pores 510, 520, 530. Shown are representative images from three independent experiments. Bars on en face images equal 50 µm; bars on transverse sections equal 10 µm.

EC/SMC Morphological Remodeling is Altered in Atheroprone Flow.

Figure 6:
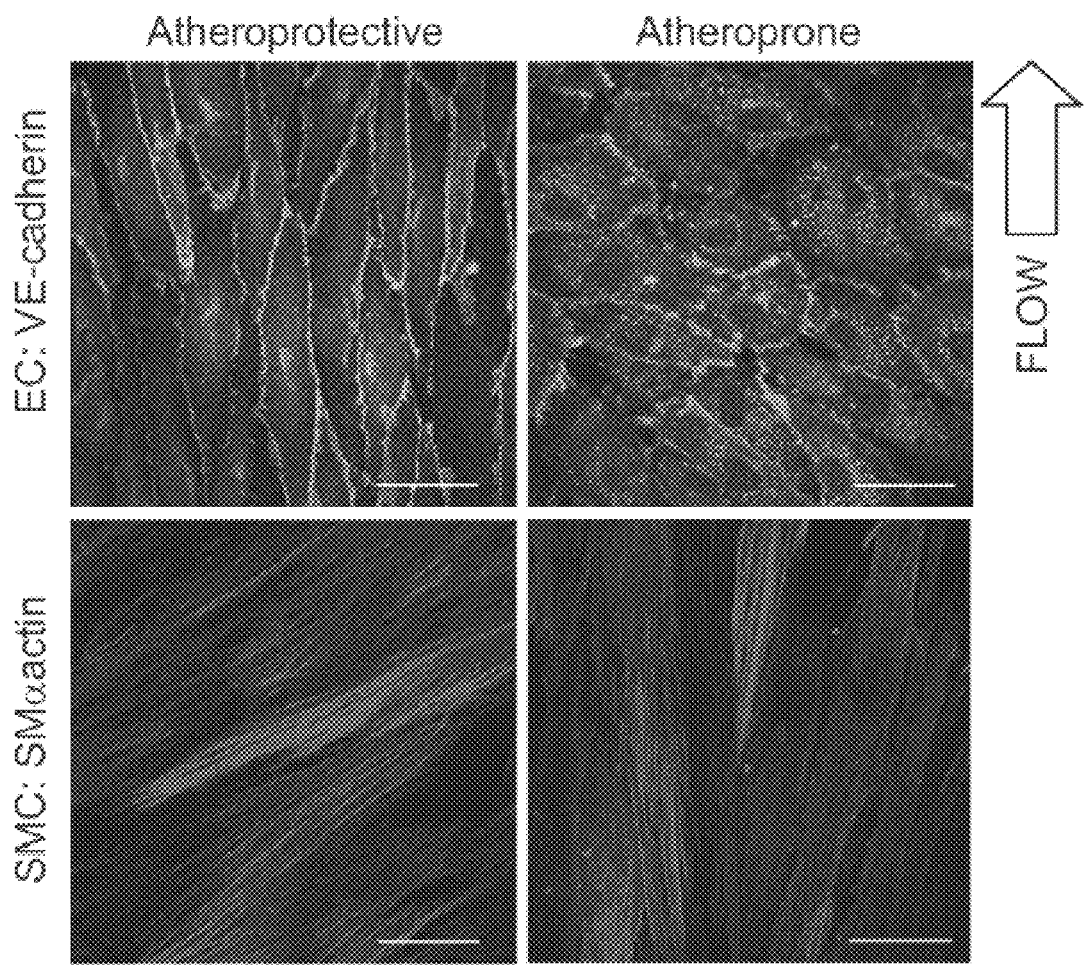
FIG. 6 shows exemplary immunofluorescence images of EC/SMC morphology and orientation.
Figure 7:
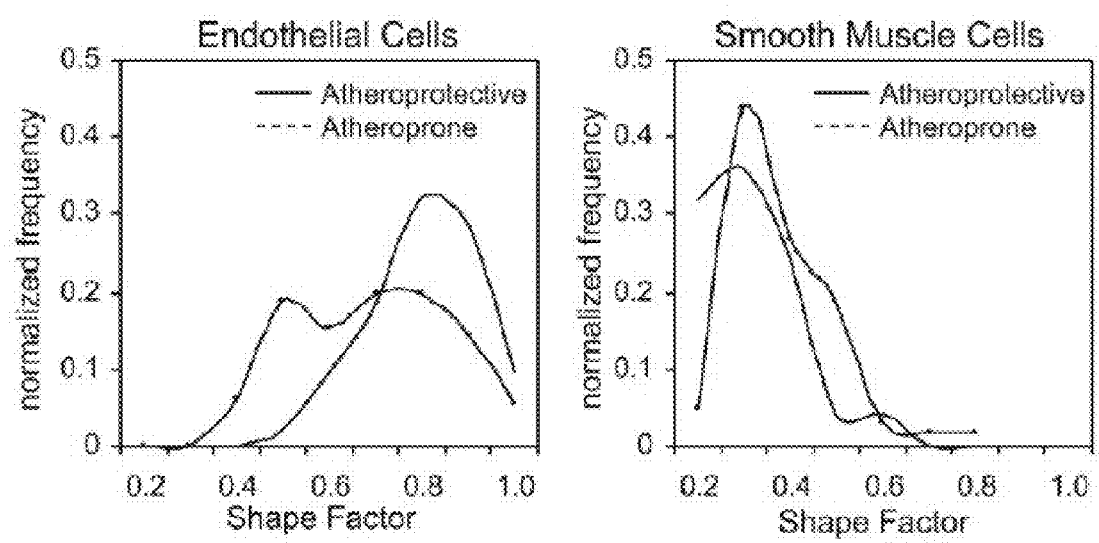
FIG. 7 shows exemplary normalized histogram plots of shape factors (SF) for ECs and SMCs.
Figure 8:
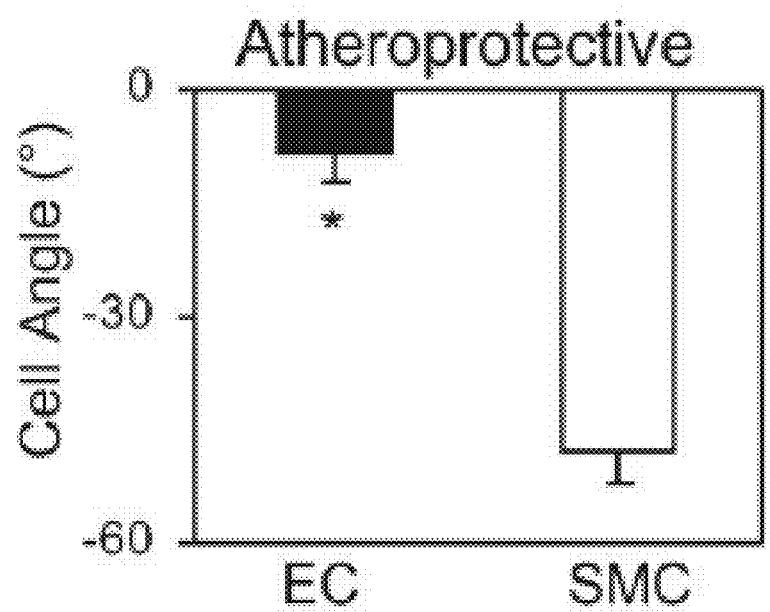
FIG. 8 shows average angles of direction for SMCs and ECs relative to the direction of atheroprotective flow (0°)

The morphology of ECs and SMCs in vivo is highly ordered, with ECs being elongated and aligned with the direction of hemodynamic flow and SMCs oriented perpendicular to the long axis of the artery and direction of blood flow. However, the endothelium in regions of complex flow, such as in arterial bifurcations, is more polygonal and less aligned, and SMCs do not consistently align perpendicular to flow. To determine whether hemodynamic flow on the endothelium induces morphological changes to ECs and SMCs, the following SF measurements for both cell types were determined: 1) alterations in elongation and 2) orientation angle measurements relative to the direction of flow. Significant differences in both cell shape (SF) and cell orientation were observed after the application of atheroprone flow compared with atheroprotective flow as shown in FIGS. 6-8. SF indicates the extent of cellular elongation, where a value of 1 specifies a circle (i.e., no elongation) and a value closer to 0 specifies an elongated cell. Representative IF images are shown in FIG. 6. As previously established, ECs exposed to atheroprone flow maintained a more polygonal shape (SF=0.75±0.002), whereas ECs under atheroprotective conditions were more elongated (SF=0.64±0.015). EC/SMC morphology and orientation were determined by immunofluorescence following flow. ECs were stained for vascular endothelial cadherin (VE-cadherin) and SMCs were stained for smooth muscle α-actin (SMαA). The arrow in FIG. 6 indicates the direction of net flow and the bars equal 50 μm.

FIG. 7 shows the distribution of EC SF normalized to the number of cells analyzed. The alignment of ECs coincided with the direction of flow when exposed to atheroprotective flow (angle relative to flow=8.6±4.01°; FIG. 8), whereas no preferential polarity of ECs under atheroprone flow could be measured due to the rounded morphology.

Figure 9:
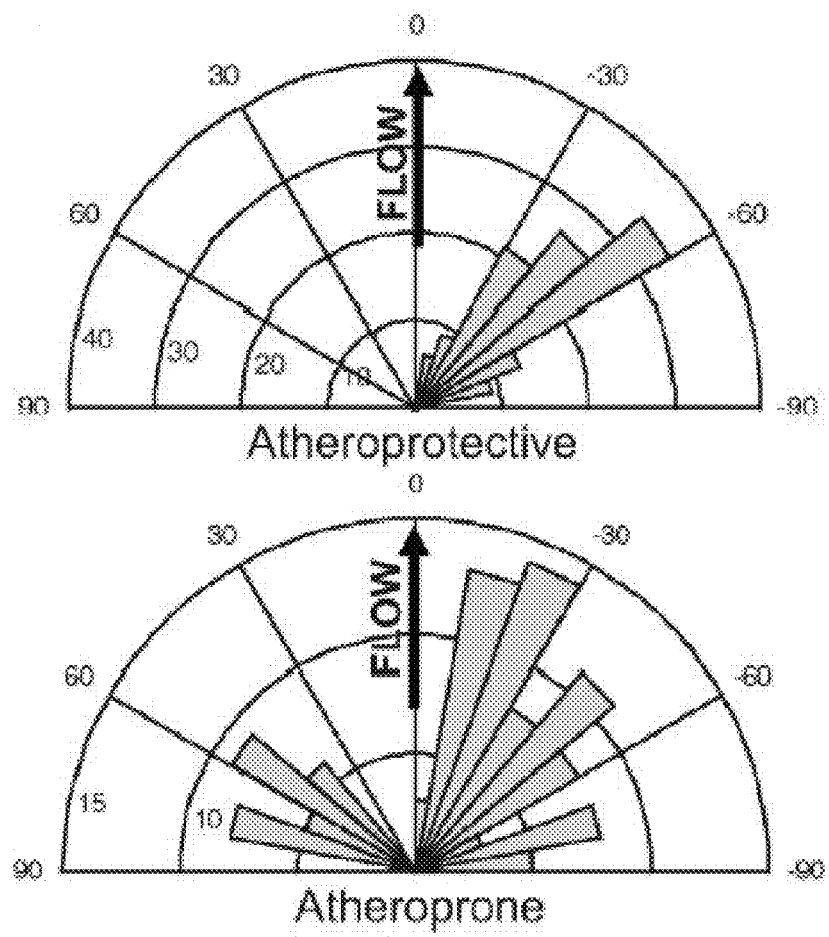
FIG. 9 shows orientation histograms of SMC direction (or angle) relative to the direction of flow.

SMCs on the TRANSWELL exposed to atheroprone flow showed a significant but small increase in elongation (SF=0.26±0.009) than those exposed to atheroprotective flow (SF=0.31±0.01 8; FIGS. 6 and 7). Interestingly, SMCs in atheroprotective flow consistently aligned more toward a perpendicular orientation relative to the direction of flow (FIGS. 8 and 9), whereas, in contrast, SMCs under atheroprone conditions exhibited a more random, less coordinated orientation (−47.9±1.3° vs. −13.1±5.0°, respectively, $P<0.0001$). FIG. 6 shows representative images of SMC orientation relative to flow, and FIG. 9 shows the histogram distribution of SMC orientation.

Purity of RNA and Protein Isolation from ECs/SMCs Following Hemodynamic Flow.

Figure 11:
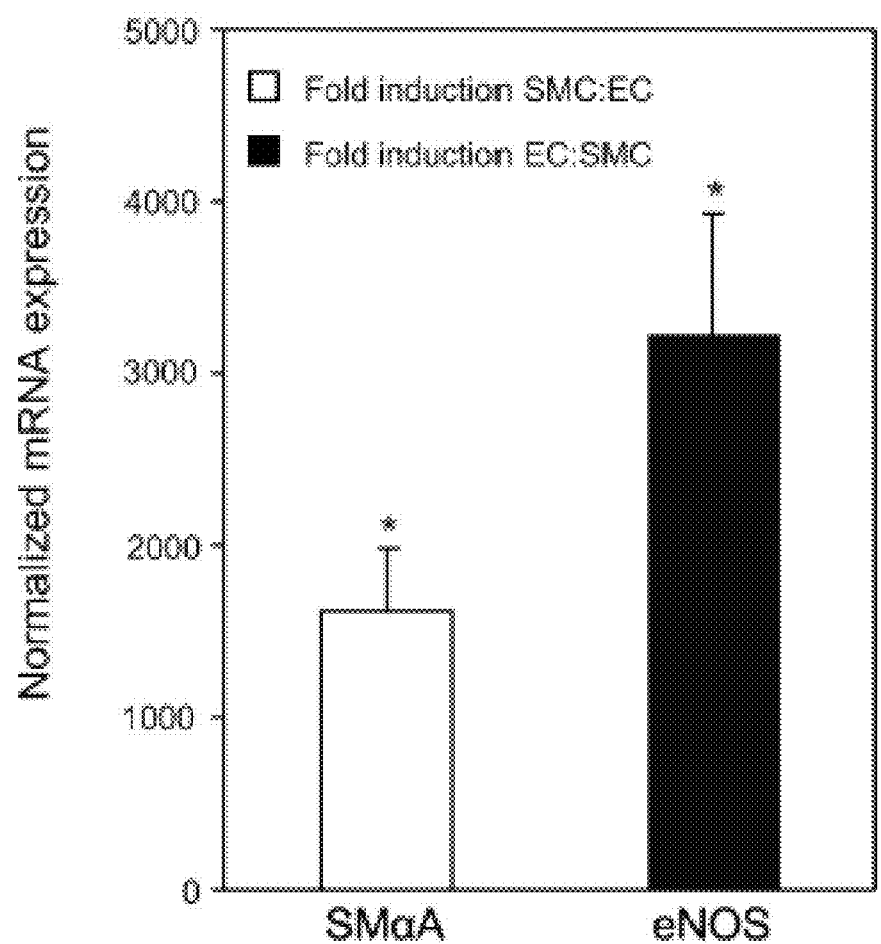
FIG. 11 shows an exemplary graph of normalized mRNA expression.
Figure 12:
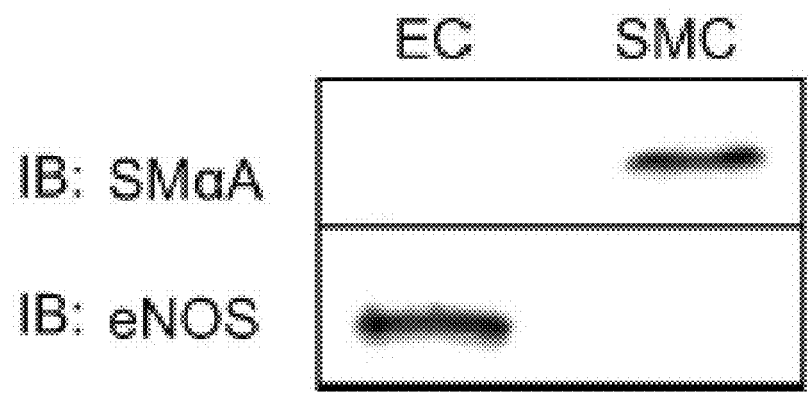
FIG. 12 shows the results of an exemplary protein analysis.

The purity of collected RNA and protein from each cell layer following the flow experiment was assessed by real-time RT-PCR and Western blot analysis for the presence of EC- and SMC-specific proteins (eNOS and SMαA, respectively; FIG. 11 and FIG. 12). No cross-contamination at the mRNA or protein level was detectable.

FIG. 11 shows real-time RT-PCR on EC and SMC populations following twenty-four hours of atheroprotective flow. Both cell types expressed respective SMC and EC markers [SMαA and endothelial nitric oxide synthse (eNOS), respectively] after the isolation of each cell type. SMCs expressed significantly larger quantities of SMαA than ECs, and the EC expression of eNOS was significantly greater than that of SMCs after CCA flow, showing that the populations of cells analyzed for differential gene regulation were pure. Values are mean±SE; n=3; *$P>0.05$.

FIG. 12 shows protein analysis confirming that only SMCs express SMαA and only ECs express eNOS. IB, immunoblot analysis.

Atheroprone Flow Differentially Regulates EC and SMC Phenotypes and Promotes Pro Inflammatory Priming.

The major goal was to determine whether differential humanderived hemodynamic flow patterns applied to ECs influence SMC phenotypic modulation. Given this objective, changes in established markers indicating EC and SMC phenotypic modulation were examined twenty-four hours after the application of atheroprone or atheroprotective flow. Genes of interest were classified as EC- or SMC-specific cell markers (EC: eNOS, Tie2, and KLF2/KLF4; SMC: SMαA, SMMHC, and myocardin) or inflammatory markers (VCAM-1, IL-8, and MCP-1). Additionally, protein analysis was performed on a subset of markers (eNOS, SMαA, VCAM-1, and PCNA). Modulation of genes and proteins was determined by the relative change in atheroprone compared with atheroprotective flow.

Figure 15:
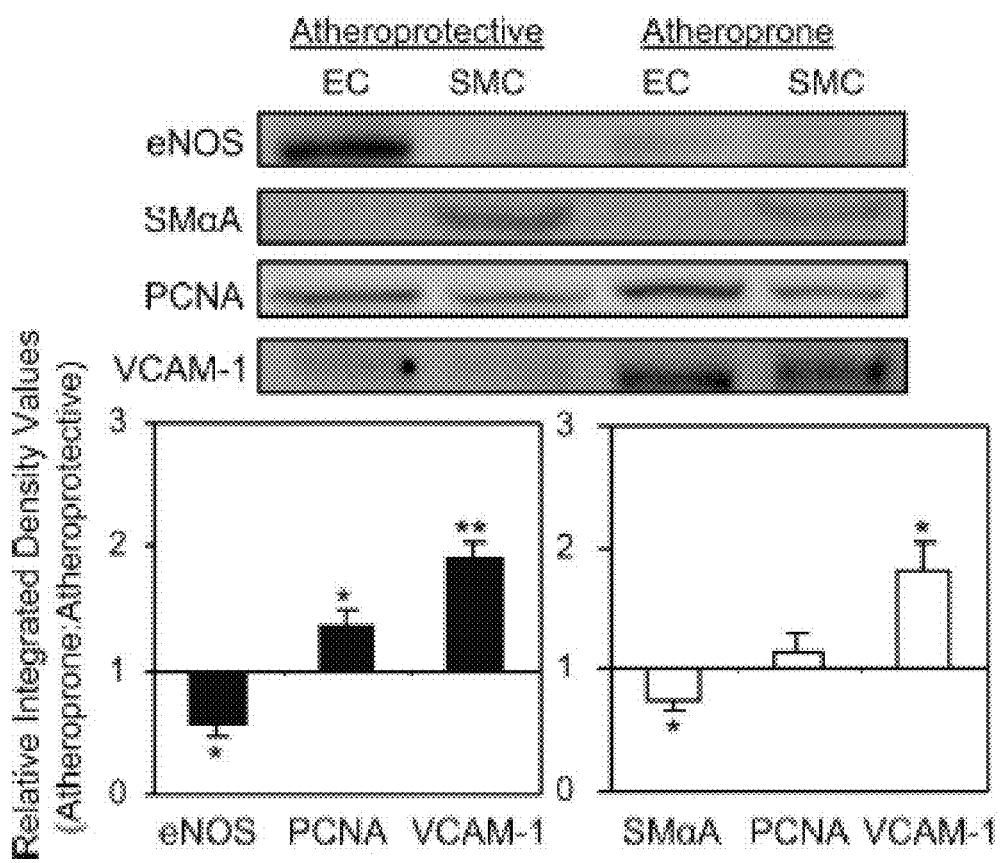
FIG. 15 shows the results of an exemplary blot analysis.

Consistently, significant reductions in mRNA levels of EC quiescent markers eNOS, Tie2, KLF2, and KLF4 were observed in response to atheroprone flow (FIG. 13), which was also confirmed by changes in protein levels of eNOS (FIG. 15). Modulation of these EC markers has previously been demonstrated via shear stress stimuli relating to atherosclerosis; however, such a comprehensive examination of EC phenotype has never occurred in the presence of SMCs for hemodyanamic flow patterns.

Figure 13:
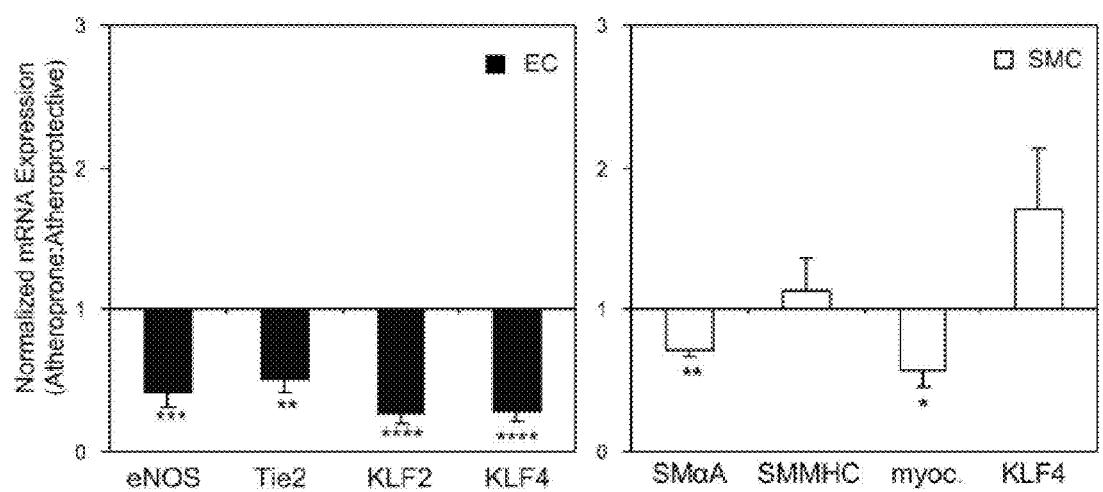
FIG. 13 shows an exemplary graph of normalized mRNA expression.

Classic SMC differentiation markers have never before been analyzed for gene modulation in a coculture model exposed to any shear stress stimulus. Hallmarks of SMC phenotypic modulation associated with atherosclerosis included a decrease in genes defining the quiescent contractile phenotype (e.g., SMαA, SMMHC, and myocardin), an increase in genes associated with the synthetic phenotype (e.g., KLF4 and VCAM-1), and the initiation of proliferative and migratory events. In the presence of atheroprone flow, SMCs showed a significant reduction in SMC differentiation markers SMαA and myocardin (FIG. 13). Protein analysis further confirmed this observation for SMαA (FIG. 15). Although the transcription factor KLF4, which was recently discovered to be important in suppressing myocardin-dependent transcription, was not significantly induced ($P=0.10$) for atheroprone relative to atheroprotective flow, this trend may still point toward a mechanism of regulating SMC phenotypic switching. Since vascular injury maximally induced KLF4 after just 4 h, it is possible that at twenty-four hours of flow, the maximal response of KLF4 was missed. Notably, SMMHC was not significantly modulated ($P=0.62$).

Figure 14:
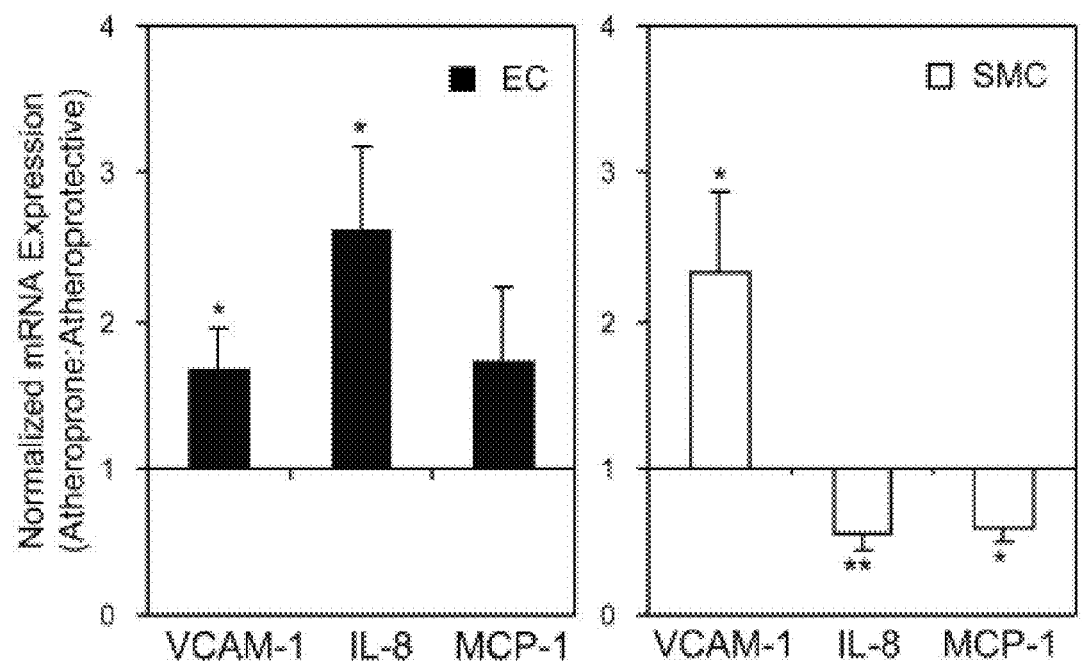
FIG. 14 shows an exemplary graph of normalized mRNA expression.
Figure 16:
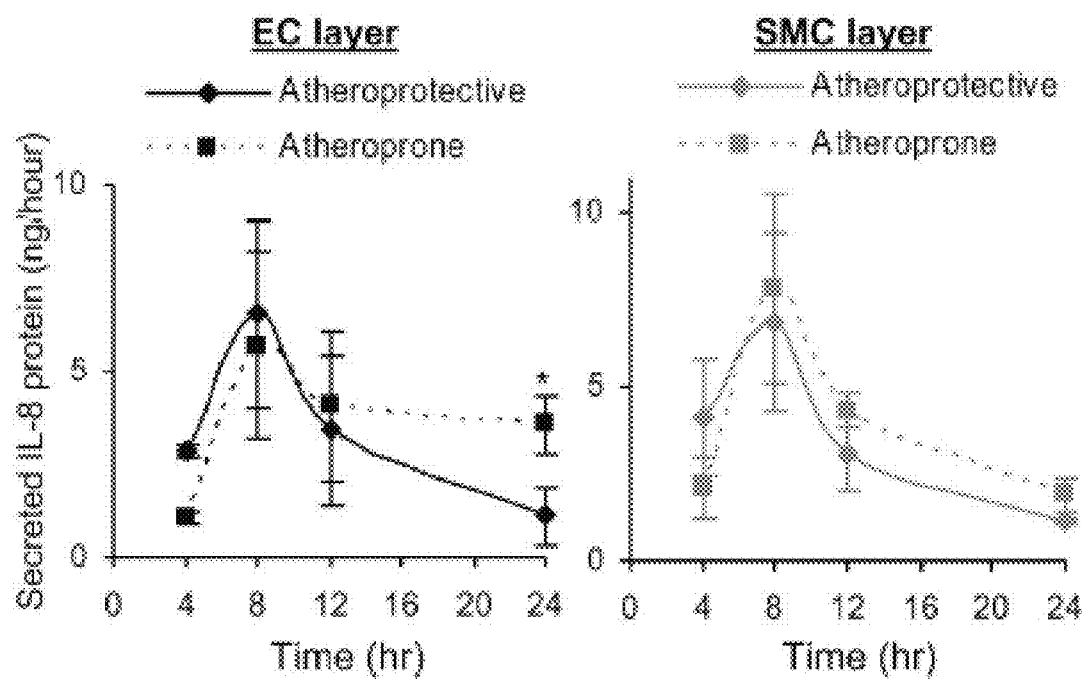
FIG. 16 shows the results of an exemplary ELISA analysis for IL-8 performed on atheroprone and atheroprotective flow-conditioned media.

Most interesting was that the reduction in EC quiescent markers and SMC contractile markers corresponded with the upregulation of several proinflammatory genes. VCAM-1 was significantly upregulated in both ECs and SMCs at both the mRNA and protein level (FIGS. 14 and 15). A significant increase in IL-8, a proinflammatory gene downstream of NF-κB activation, was also observed in ECs at the mRNA level. Secretion of IL-8 from EC and SMC layers was further measured as a function of time during the application of both flow patterns and was only significantly augmented in ECs during later time points of atheroprone flow (FIG. 16). In contrast, decreases in IL-8 and MCP-1 were concurrently observed in SMCs (FIG. 14). Finally, analysis of the proliferative marker PCNA showed increased protein levels in ECs exposed to atheroprone flow but no change for SMCs (FIG. 15).

Figure 17:
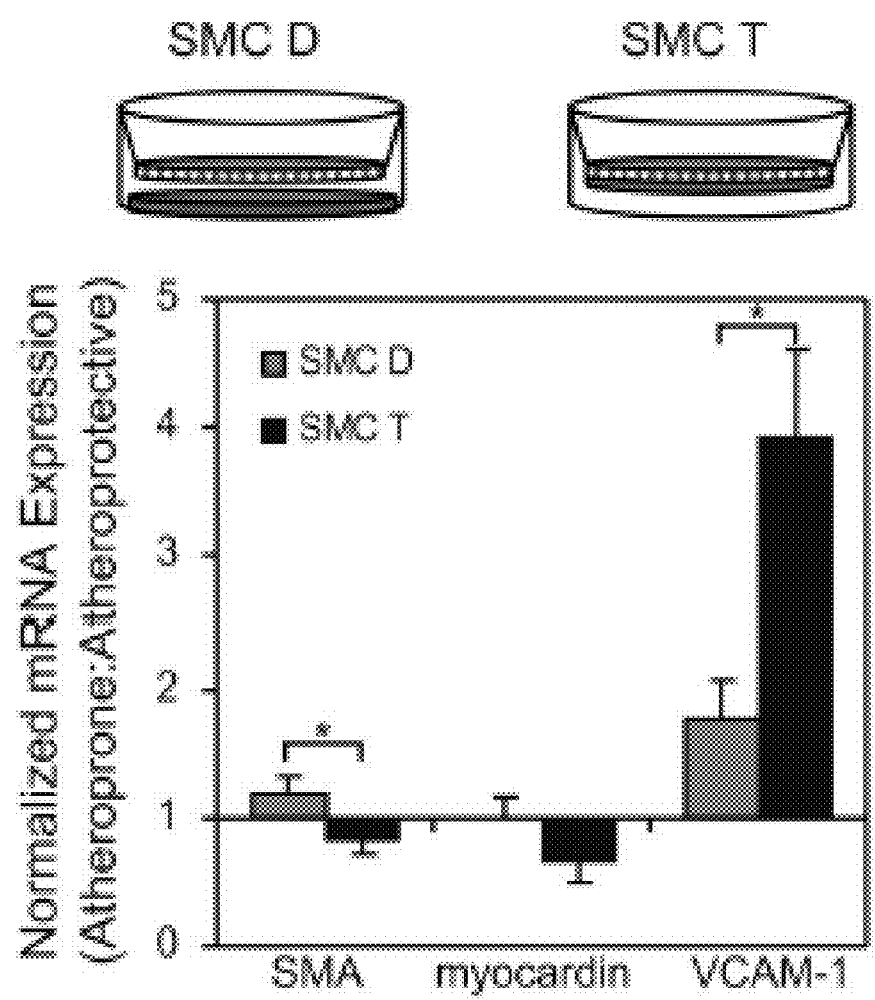
FIG. 17 shows an exemplary graph of normalized mRNA expression.
Figure 18:
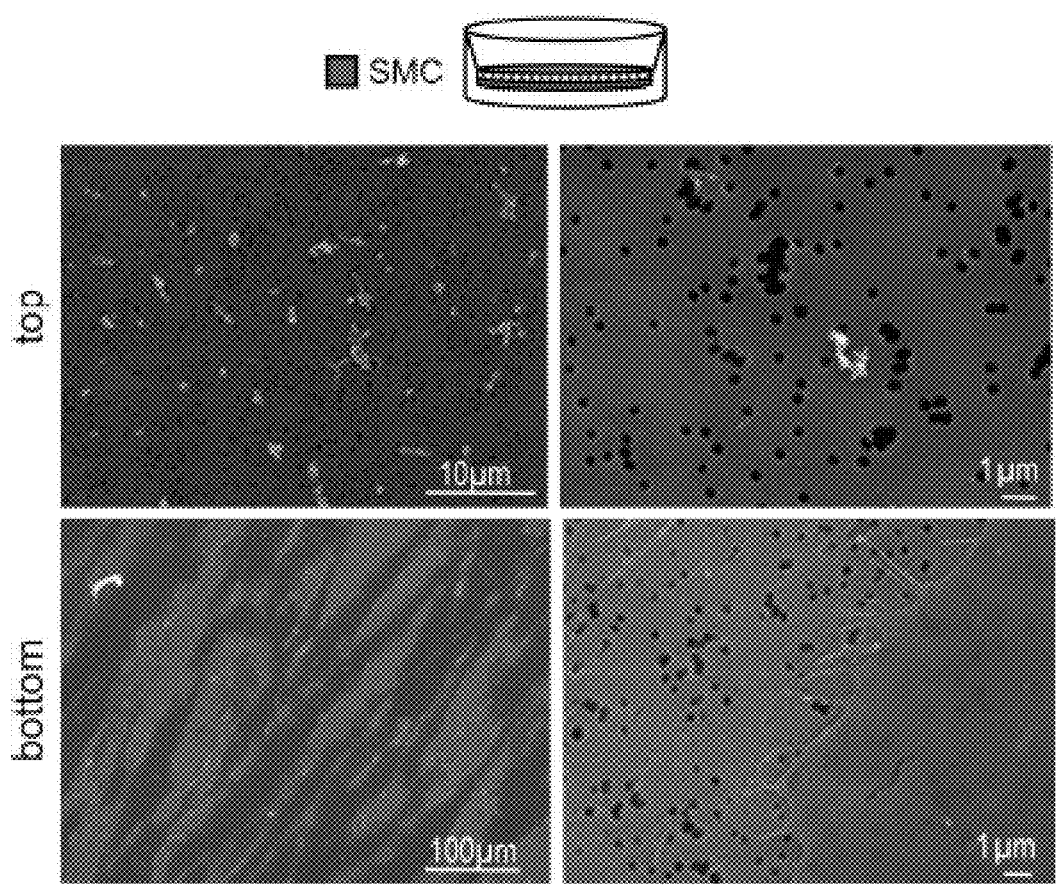
FIG. 18 shows an exemplary scanning electron micrograph of the surfaces of the membrane.

To control for a flow-induced EC influence on the SMC response, SMCs were plated under two conditions in monoculture: 1) on the bottom of the TRANSWELL holding dish in the presence of a TRANSWELL membrane (SMC D) or 2) on the bottom of the TRANSWELL membrane (SMC T), as shown in FIG. 17. For each condition, flow was applied to the top of the TRANSWELL membrane without ECs. Real-time RT-PCR analysis of samples showed that significant differences existed between each condition for SMaA and VCAM-1 but not for myocardin (FIG. 17). VCAM-1 was the only gene appreciably inducted by atheroprone flow for both conditions. Potential confounding factors introduced for the SMC T condition were smooth muscle cellular processes that extruded through the porous membrane to the top of the TRANSWELL where flow was being applied (FIG. 18), which was not observed in the experiments with ECs present. The significant changes between each condition (SMC D vs. SMC T) indicate the sensitivity of SMCs to their local environment. Thus, for this study, comparison between the two distinct flow patterns applied in the presence of both cell types was the most robust method to control for all features (e.g., media exchange, experimental setup, time in culture, and heterocellular presence) of the hemodynamic coculture environment.

Arterial Hemodynamics Control Epigenetic Regulation of SMC Gene Expression.

Figure 19:
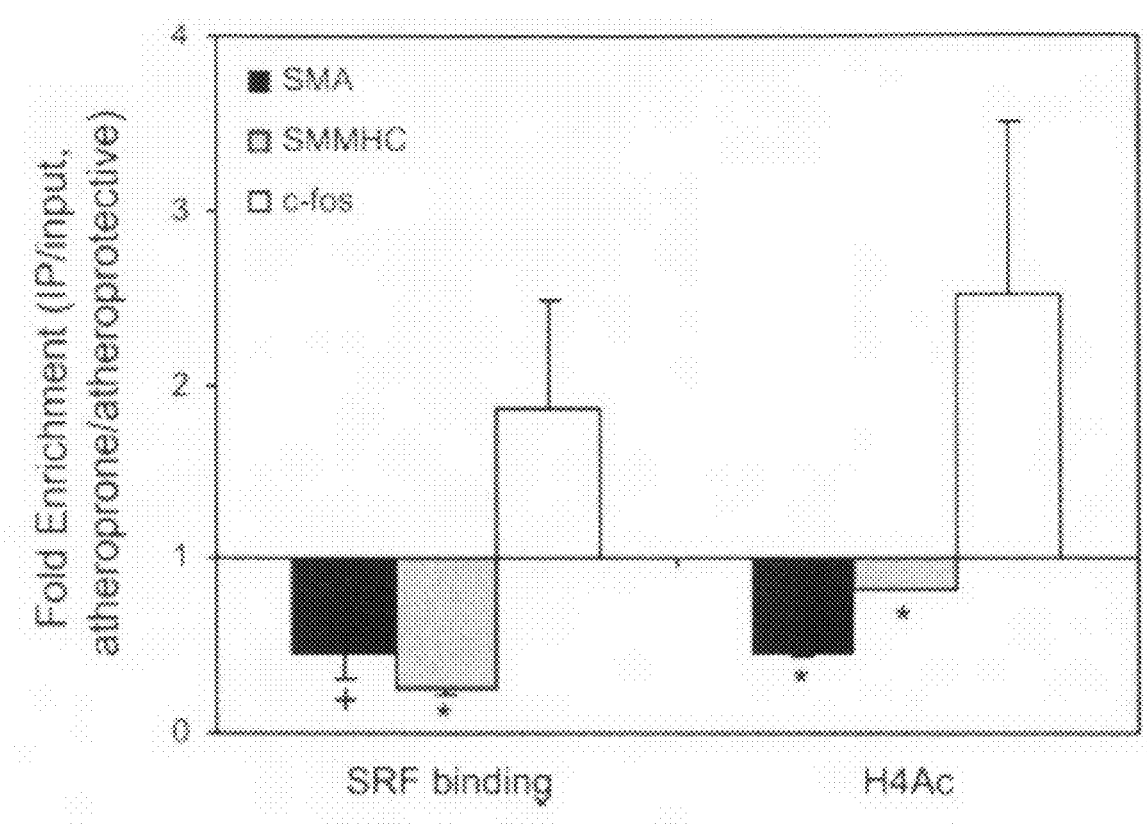
FIG. 19 shows a graph of exemplary fold enrichment.

Many of the promoter regions of genes that encode SMC-selective contractile proteins contain CArG cis-regulatory elements that bind SRF, including SMαA and SMMHC. ChIP experiments were conducted to determine whether SRF binding and histone H4 acetylation in 5'-CArG promoter regions of the SMαA, SMMHC, and c-fos promoters were regulated at the epigenetic level by hemodynamic flow. The results indicated a reduction of histone H4 acetylation and SRF binding in response to atheroprone flow relative to atheroprotective flow for SMαA and SMMHC (FIG. 19). Conversely, histone H4 acetylation and SRF binding to the c-fos CArG region was not statistically different among flow conditions (FIG. 19). This epigenetic fingerprint was identical to in vitro experiments in SMCs in response to PDGF-BB and in vivo in response to acute vascular injury.

Drugs

The drug may be selected from a group comprising actinomycin-D, batimistat, c-myc antisense, dexamethasone, paclitaxel, taxanes, sirolimus, tacrolimus and everolimus, unfractionated heparin, low-molecular weight heparin, enoxaprin, bivalirudin, tyrosine kinase inhibitors, GLEEVEC (imatinib), wortmannin, PDGF inhibitors, AG1295, rho kinase inhibitors, Y27632, calcium channel blockers, amlodipine, nifedipine, and ACE inhibitors, synthetic polysaccharides, ticlopinin, dipyridamole, clopidogrel, fondaparinux, streptokinase, urokinase, r-urokinase, r-prourokinase, rt-PA, APSAC, TNK-rt-PA, reteplase, alteplase, monteplase, lanoplase, pamiteplase, staphylokinase, abciximab, tirofiban, orbofiban, xemilofiban, sibrafiban, roxifiban, an anti-restenosis agent, an anti-thrombogenic agent, an antibiotic, an anti-platelet agent, an anti-clotting agent, an anti-inflammatory agent, an anti-neoplastic agent, an anti-hypertensive agent, a chelating agent, penicillamine, triethylene tetramine dihydrochloride, EDTA, DMSA (succimer), deferoxamine mesylate, a cholesterol lowering agent, a statin, an agent that raises HDL, a cyclyoxygenase inhibitor, Ccicbrcx CELEBREX (celecoxib), VIOXX (rofecoxib), a radiocontrast agent, a radio-isotope, a prodrug, antibody fragments, antibodies, live cells, therapeutic drug delivery microspheres or microbeads, and any combinations thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

The invention claimed is:

1. A method of testing a drug or a compound for an effect on the vascular system, said method comprising:
adding a culture media to a Petri dish;
adding a drug or a compound to the culture media;
plating a first cell type on a first side of a porous membrane,
plating a second cell type on a second side of the porous membrane, wherein said porous membrane is suspended in the Petri dish such that the first side is proximal and in spaced relation to a surface of the Petri dish, thereby defining within the Petri dish a lower volume comprising the first cell type and an upper volume comprising the second cell type, the porous membrane being adapted to permit fluid communication of the culture media and physical interaction and communication between cells of the first cell type and cells of the second cell type, and all of the cell types are within the culture media;
perfusing culture media into and out of the upper volume;
perfusing culture media into and out of the lower volume;
applying a shear force upon the plated second cell type, said shear force resulting from flow of the culture media induced by a hemodynamic flow device, said flow mimicking hemodynamic flow; and
comparing at least one of the first cell type and the second cell type after applying the shear force for a period of time to at least one of the first cell type and the second cell type after applying the shear force for the period of time wherein the media does not include the drug or compound, to determine the effect of the drug or compound on at least one of the first cell type and the second cell type.

2. The method of claim 1, where the drug or the compound is added to the culture media while applying the shear force.

3. The method of claim 1, where the drug or the compound is added to the culture media before applying the shear force.

4. The method of claim 1, wherein the drug is a cyclooxygenase inhibitor; a taxane; a tyrosine kinase inhibitor; a low molecular weight heparin; an anti-thrombogenic agent; a calcium channel blocker; an anti-platelet agent; an anticlotting agent; a chelating agent; an anti-inflammatory agent; a rho kinase inhibitor; a PDGF inhibitor, a cholesterol lowering agent; an anti-restenosis agent; an antibiotic; an anti-neoplastic agent; an anti-hypertensive agent; a synthetic polysaccharide; an agent that raises HDL; or a combination thereof.

5. The method of claim 4, wherein the cyclooxygenase inhibitor is celecoxib; the taxane is paclitaxel; the tyrosine kinase inhibitor is imatinib; the low molecular weight heparin is enoxaparin; the anti-thrombogenic agent is bivalirudin, dipyridamole, urokinase, r-urokinase, r-prourokinase, reteplase, alteplase, streptokinase, rt-PA, TNK-rt-PA, monteplase, staphylokinase, pamiteplase, unfractionated heparin, or APSAC; the calcium channel blocker is amlodipine or nifedipine; the anti-platelet agent is clopidogrel, abciximab, tirofiban, orbofiban, xemilofiban, sibrafiban, roxifiban or ticlopinin; the anticlotting agent is fondaparinux; the chelating agent is penicillamine, triethylene tetramine dihydrochloride, EDTA, DMSA, deferoxamine mesylate or batimastat; the anti-inflammatory agent is rofecoxib; the rho kinase inhibitor is Y27632; the PDGF inhibitor is AG1295; the cholesterol lowering agent is a statin; the antibiotic is actinomycin-D; the anti-neoplastic agent is c-myc antisense or dexamethasone; or the anti-hypertensive agent is an ACE inhibitor.

6. The method of claim 1 wherein the drug is atorvastatin, sirolimus, tacrolimus, everolimus, wortmannin, or a combination thereof.

7. The method of claim 1, wherein the drug or the compound is a radiocontrast agent, a radio-isotope, a prodrug, an antibody fragment, an antibody, a live cell, a therapeutic drug delivery microsphere or microbead, or a combination thereof.

8. The method of claim 1 wherein the compound is capable of inhibiting, activating or altering the function of proteins or genes in said cell types.

9. The method of claim 1, further comprising the step of culturing all the cell types.

10. The method of claim 1, wherein said at least one of the first cell type and the second cell type is analyzed for toxicity, inflammation, permeability, compatibility, cellular adhesion or phenotypic modulation resulting from the drug or the compound.

11. The method of claim 1, wherein at least one of the first cell type and the second cell type are vascular or organ cells from one or more patients with an identified genotype linked to drug toxicity or a pathophysiological endpoint.

12. The method of claim 11, wherein said one or more patients have a single nucleotide polymorphism linked to drug toxicity or a pathophysiological endpoint.

13. The method of claim 1, wherein said first cell type is renal cells, cells of the airways, or cells of the blood-brain-barrier blood-brain barrier, and said second cell type is vascular cells.

14. The method of claim 1, wherein the hemodynamic flow is derived from a previously measured hemodynamic pattern.

15. The method of claim 14, wherein the previously measured hemodynamic pattern is human derived.

16. The method of claim 15, wherein said pattern is derived from a patient having a pathological condition.

17. The method of claim 1, wherein said hemodynamic flow is time-variant.

18. The method of claim 1, wherein the first cell type is smooth muscle cells, glial cells, astrocytes, neurons, or epithelial podocytes.

19. The method of claim 18, wherein the second cell type is endothelial cells.

20. The method of claim 1 further comprising:
modeling a hemodynamic pattern into a set of electronic instructions; and
applying the shear force upon the plated second cell type based on the set of electronic instructions.

21. The method of claim 20, wherein said hemodynamic pattern is derived from analysis of ultrasound data.

22. The method of claim 20, wherein said hemodynamic pattern is derived from analysis of magnetic resonance imaging (MRI) data.

23. The method of claim 20, wherein said hemodynamic pattern is time-variant.

24. The method of claim 20, wherein the set of electronic instructions is accepted by an electronic controller of a hemodynamic flow device, the electronic controller operating a motor of the device, and the motor causing rotation of a cone connected to the motor, wherein said rotation of the cone results in said flow of the culture media.

25. The method of claim 1, wherein the shear force is applied by a device for mimicking hemodynamic flow during cell culture, said device comprising:
   an electronic controller for receiving a set of electronic instructions;
   a motor operated by the electronic controller; and
   a shear force applicator operatively connected to the motor for being driven by the motor.

26. The method of claim 25, wherein the shear force applicator comprises a cone attached to the motor.

27. The method of claim 25, wherein the device further comprises inlets and outlets within the portions of the Petri dish defining the upper and lower volumes.

28. The method of claim 1, wherein the compound is a vascular stent material and the method further comprises testing at least one of the cell types for compatibility with, cellular adhesion to, or phenotypic modulation by the vascular stent material.

29. The method of claim 28, wherein the vascular stent material comprises a nanoporous metal, a polymer, or a carbon material.

30. The method of claim 28, wherein the drug or compound is eluted from a vascular stent material adjacent to the second cell type.

31. The method of claim 1, wherein the method further comprises perfusing the drug or compound into at least one of the upper volume and the lower volume.

32. The method of claim 1, further comprising either plating a third cell type on the surface of the Petri dish, or suspending a third cell type in the culture media in the lower volume.

33. The method of claim 32, further comprising the step of culturing all of the cell types.

34. The method of claim 32, further comprising the step of comparing at least one of the first cell type, the second cell type and the third cell type after applying the shear force for a period of time to at least one of the first cell type, the second cell type and the third cell type after applying the shear force for the period of time wherein the media does not include the drug or compound, to determine the effect of the drug or compound on at least one of the first cell type, the second cell type and the third cell type.

35. The method of claim 32, wherein the hemodynamic flow is derived from a previously measured hemodynamic pattern.

36. The method of claim 35, wherein the previously measured hemodynamic pattern is human derived.

37. The method of claim 32, wherein the first cell type is smooth muscle cells, glial cells, astrocytes, neurons, or epithelial podocytes.

38. The method of claim 21, wherein the second cell type is endothelial cells.

39. The method of claim 32, wherein the third cell type is smooth muscle cells, glial cells, astrocytes, neurons, macrophages, or leukocytes.

40. The method of claim 32, wherein said first cell type and said third cell type are, renal cells, cells of the airways, or cells of the blood-brain-barrier, and wherein said second cell type is vascular cells.

41. The method of claim 26, wherein the hemodynamic pattern is from an artery, a vein or an organ.

42. The method of claim 35, wherein said hemodynamic flow is time-variant.

43. The method of claim 1, further comprising analyzing said culture media for cytokine or humoral factor secretion.

* * * * *

UNITED STATES PATENT AND TRADEMARK OFFICE
CERTIFICATE OF CORRECTION

| | | |
|---|---|---|
| PATENT NO. | : 7,811,782 B2 | Page 1 of 1 |
| APPLICATION NO. | : 12/007483 | |
| DATED | : October 12, 2010 | |
| INVENTOR(S) | : Blackman et al. | |

It is certified that error appears in the above-identified patent and that said Letters Patent is hereby corrected as shown below:

Column 30, Claim 38, Line 24: "claim 21" should read --claim 32--.

Column 30, Claim 40, Line 30: "are, renal cells" should read --are renal cells--.

Column 30, Claim 41, Line 33: "claim 26" should read --claim 36--.

Signed and Sealed this
Thirty-first Day of May, 2011

David J. Kappos
*Director of the United States Patent and Trademark Office*

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
agcattcggg ccgagatgtc t                                          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ctccattaag aggagcggct c                                          21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
catgacttcc aagctggccg                                            20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaccgccac tcacacctg                                                19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggccagaatt ggacccggtg tac                                           23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccagcagcaa gtgtcccaaa g                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcagctcca aatcctcagc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cactgtcagg aatcctgtga                                               20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agatggttct gaggaggaaa cg                                            22

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgttaatca ctatgaggct tggc                                              24

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtttgtcagg ctaagttaca tattgatga                                         29

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agcagaacag aggaatgcag tggaagagac                                        30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgcgcggga ccatatttag tcaggggag                                         30

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccgcactgc accctcggtg                                                   20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgctggatg acgtgagtaa acct                                              24

<210> SEQ ID NO 16
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctaagctggt aggtgcctgt g                                              21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttatgaatt ctcagccctc                                                20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgcagccgt cccagttg                                                  18

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctgcctttg ctgacgctga tga                                            23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgcttgtcca ggtggtccat g                                              21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcagtggcgt tgaagaagag tt                                             22

<210> SEQ ID NO 22
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaagccggc cttacaga                                                      18

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaactgtag aaagttgctt attcact                                            27

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgaagcgtc tcacaggtcc a                                                  21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gggcaacatt gacataaagt gttt                                               24

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcccactc gcctcccaaa caaggagc                                           28

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgggcggga gacaacccaa aaaggccagg                                         30

<210> SEQ ID NO 28
<211> LENGTH: 25
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 28
tacagggaaa ggccgtggaa acctg                                              25
```